(12) United States Patent
Brenner et al.

(10) Patent No.: US 8,221,389 B2
(45) Date of Patent: Jul. 17, 2012

(54) LOW PROFILE ADAPTOR FOR USE WITH A MEDICAL CATHETER

(75) Inventors: Laurence D. Brenner, Northborough, MA (US); William L. Churchill, Worcester, MA (US); Patrice A. Weststrate, Norwood, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1760 days.

(21) Appl. No.: 11/313,028

(22) Filed: Dec. 19, 2005

(65) Prior Publication Data

US 2006/0100604 A1 May 11, 2006

Related U.S. Application Data

(63) Continuation of application No. 10/141,909, filed on May 9, 2002, now Pat. No. 6,976,980.

(51) Int. Cl.
*A61M 1/00* (2006.01)
*A61M 5/00* (2006.01)
*A61M 25/16* (2006.01)
*A61M 25/18* (2006.01)

(52) U.S. Cl. ............ 604/537; 604/32; 604/248

(58) Field of Classification Search ............ 604/104, 604/105, 108, 174, 175, 246–256, 264, 533–539, 604/30–34
See application file for complete search history.

(56) References Cited

U.S. PATENT DOCUMENTS

| | | |
|---|---|---|
| 3,926,187 A | 12/1975 | Iglesias |
| 4,306,545 A | 12/1981 | Ivan et al. |
| 4,390,017 A | 6/1983 | Harrison et al. |
| 4,417,890 A | 11/1983 | Dennehey et al. |
| 4,424,833 A | 1/1984 | Spector et al. |
| 4,473,369 A | 9/1984 | Lueders et al. |
| 4,557,261 A | 12/1985 | Rugheimer |
| 4,774,944 A | 10/1988 | Mischinski |
| 4,826,477 A | 5/1989 | Adams |

(Continued)

FOREIGN PATENT DOCUMENTS

EP 976418 A1 2/2000

(Continued)

OTHER PUBLICATIONS

International Search Report for PCT Application No. PCT/US03/14782 (the corresponding PCT application to the present application) mailed Oct. 2, 2003.

*Primary Examiner* — Matthew F DeSanto
(74) *Attorney, Agent, or Firm* — Kenyon & Kenyon LLP

(57) ABSTRACT

An adaptor for use with a medical catheter comprises a housing having a first tubular channel with a first longitudinal axis, a dial having a second tubular channel with a second longitudinal axis, and an adaptor fitting removably connected to the second tubular channel. The dial is rotatable between an open position and a closed position when the adaptor fitting is connected thereto. In the open position the first tubular channel is fluidly connected to the second tubular channel, and in the closed position the first tubular channel is not fluidly connected to the second tubular channel. The dial may be configured such that it is not rotatable between the open position and the closed position when the adaptor fitting is not connected thereto. The housing may comprise an upper housing member, an intermediate housing member, and a lower housing member.

17 Claims, 15 Drawing Sheets

U.S. PATENT DOCUMENTS

| | | |
|---|---|---|
| 4,834,712 A | 5/1989 | Quinn et al. |
| 4,863,438 A | 9/1989 | Gauderer et al. |
| 4,944,732 A | 7/1990 | Russo |
| 5,007,900 A | 4/1991 | Picha et al. |
| 5,026,352 A | 6/1991 | Anderson |
| 5,071,405 A | 12/1991 | Piontek et al. |
| 5,100,394 A | 3/1992 | Dudar et al. |
| 5,112,310 A | 5/1992 | Grobe |
| 5,158,569 A | 10/1992 | Strickland et al. |
| 5,167,627 A | 12/1992 | Clegg et al. |
| 5,259,399 A | 11/1993 | Brown |
| 5,267,983 A | 12/1993 | Oilschlager et al. |
| 5,273,529 A | 12/1993 | Idowu |
| 5,290,249 A | 3/1994 | Foster et al. |
| 5,290,250 A | 3/1994 | Bommarito |
| 5,358,488 A | 10/1994 | Suriyapa |
| 5,488,949 A | 2/1996 | Kreifels et al. |
| 5,549,657 A | 8/1996 | Stern et al. |
| 5,720,734 A | 2/1998 | Copenhaver et al. |
| 5,836,924 A * | 11/1998 | Kelliher et al. ............... 604/248 |
| 5,882,348 A * | 3/1999 | Winterton et al. ............ 604/537 |
| 6,019,746 A | 2/2000 | Picha et al. |
| 6,095,997 A | 8/2000 | French et al. |
| 6,458,106 B1 | 10/2002 | Meier et al. |
| 6,569,117 B1 | 5/2003 | Ziv et al. |
| 6,620,124 B1 * | 9/2003 | Peavey ............................ 604/32 |
| 6,976,980 B2 * | 12/2005 | Brenner et al. ............... 604/535 |
| 6,979,322 B2 * | 12/2005 | Chu et al. ...................... 604/248 |
| 2001/0007067 A1 | 7/2001 | Kurfess et al. |
| 2002/0177806 A1 | 11/2002 | Meier et al. |

FOREIGN PATENT DOCUMENTS

| | | |
|---|---|---|
| WO | 0040291 A1 | 7/2000 |

\* cited by examiner

LOW PROFILE ADAPTOR FOR USE WITH A MEDICAL CATHETER

CROSS-REFERENCE TO RELATED APPLICATIONS

The present application is a continuation of U.S. patent application Ser. No. 10/141,909, inventors Laurence D. Brenner et al., filed May 9, 2002, now U.S. Pat. No. 6,976,980 which is incorporated herein by reference.

BACKGROUND OF THE INVENTION

The present invention relates generally to medical catheters, such as gastrostomy feeding tubes, and relates more particularly to low profile adaptors well-suited for use with medical catheters.

Certain patients are unable to take food transorally due to an inability to swallow. Such an inability to swallow may be due to a variety of reasons, such as esophageal cancer, neurological impairment and the like. Although the intravenous administration of food and/or medications to such patients may be a viable short-term approach, it is not well-suited for the long-term. Accordingly, the most common approach to the long-term feeding of such patients involves gastrostomy, i.e., the creation of a feeding tract or stoma between the stomach and the upper abdominal wall. Feeding is then typically performed by administering food through a feeding tube that has been inserted into the feeding tract, with the distal end of the feeding tube extending into the stomach and being retained therein by an internal anchor or bolster and the proximal end of the feeding tube extending through the abdominal wall.

Although gastrostomies were first performed surgically, most gastrostomies are now performed using percutaneous endoscopy. In one type of percutaneous endoscopic gastrostomy (PEG) technique, the distal end of an endoscope is inserted into a patient's mouth and is passed through the esophagus into the stomach. After distension of the stomach by inflation, an entry site on the abdomen is identified and an incision is made. A needle, with an outer cannula, is inserted through the entry site across the abdominal and gastric walls. While keeping the cannula in place, the needle is removed, and a flexible wire is passed through the cannula into the stomach and into a snare loop extended from the distal end of the endoscope. The endoscopic snare loop is then used to grasp the wire, the cannula is released, and the endoscope and wire are withdrawn through the esophagus and mouth of the patient. A silicone gastrostomy feeding tube, the distal end of which is attached to a silicone, dome-shaped internal bolster, is then secured to the wire and is pulled from its proximal end through the esophagus and into the stomach until the internal bolster engages the stomach wall and the feeding tube extends through the stomach and abdominal walls, with the proximal end of the feeding tube extending approximately one foot beyond the abdominal wall. (Over a period of several days following implantation of the feeding tube, a stable stoma tract forms around the feeding tube between the gastric and abdominal walls.)

With the internal bolster in place against the gastric wall, an external bolster is typically secured to the feeding tube to engage the abdomen so as to prevent longitudinal movement of the feeding tube within the stoma tract. Additionally, a "Y-port" adapter is typically attached to the proximal end of the feeding tube, the Y-port adapter being adapted to receive a pair of connector tips through which food and/or medications may be dispensed. In addition, a detachable locking clip is typically secured to the feeding tube at a point between the external bolster and the Y-port adapter to prevent gastric fluids from escaping through the proximal end of the feeding tube when the feeding tube is not in use.

Alternative techniques for implanting gastrostomy feeding tubes using percutaneous endoscopic gastrostomy are disclosed in U.S. Pat. No. 5,112,310, inventor Grobe, which issued May 12, 1992, and U.S. Pat. No. 5,167,627, inventors Clegg et al., which issued Dec. 1, 1992, both of which are incorporated herein by reference.

Although gastrostomy feeding tubes of the type described above work well for their intended purpose, many active patients find the nearly one foot length of tubing that extends externally to be unwieldy, difficult to conceal and susceptible to being inadvertently pulled on. As can readily be appreciated, these conditions are potential sources of physical and/or psychological trauma to the patient. Consequently, a variety of low-profile replacement tube assemblies (also referred to in the art as low-profile replacement PEG devices) have been designed for implantation within the stoma tract following the removal of an initially-implanted gastrostomy feeding tube. Such replacement assemblies are referred to as being "low-profile" because they are considerably more compact externally than the above-described initially-implanted gastrostomy feeding tube assemblies.

An example of a low-profile replacement PEG device is disclosed in U.S. Pat. No. 4,944,732, inventor Russo, which issued Jul. 31, 1990, and which is incorporated herein by reference. The low-profile replacement PEG device of said patent comprises a deformable, conical tip portion having at least one side aperture therethrough, a tube portion which extends rearwardly from the tip portion, a fitting portion on the rear end of the tube portion, a removable valve portion in the fitting portion and a flange portion which extends outwardly from the fitting portion. The device is adapted to be installed in a patient so that the tube portion extends through a pre-established stoma with the tip portion located in the patient's stomach and with the fitting portion and the flange portion engaging the skin of the patient adjacent the stoma.

The deformable tip portion of the above-described low-profile replacement PEG device functions as an internal bolster to anchor its associated tube portion in a patient's stomach. To implant and/or remove the aforementioned tube portion from a patient's stomach, an obturator or similar device is typically inserted through the tube portion and is used to elongate or otherwise deform the tip portion in such a way as to permit the tip portion to fit through the stoma. Removal of the obturator from the tip portion then permits the tip portion to expand to its original shape for anchoring.

Another type of low-profile replacement PEG device uses an inflatable balloon, instead of a deformable tip portion, as an internal bolster to retain the distal end of its associated tube within a patient's stomach. To implant such a device in a patient, the inflatable balloon is deflated, the distal end of the tube portion is inserted through the stoma, and the balloon is then inflated. To remove the implanted device from a patient, the balloon is deflated and the tube is then withdrawn from the stoma.

Further examples of low-profile replacement PEG devices are disclosed in U.S. Pat. No. 4,863,438, inventors Gauderer et al., which issued Sep. 5, 1989; and U.S. Pat. No. 5,720,734, inventors Copenhaver et al., which issued Feb. 24, 1998, both of which are incorporated herein by reference.

Although low-profile replacement PEG devices are less awkward and bulky than initially-implanted gastrostomy tube assemblies, the use of such low-profile replacement PEG devices suffers from its own set of shortcomings. One such shortcoming is that the implantation of a low-profile replacement PEG device must be preceded by the removal of an initially-implanted gastrostomy tube. Such removal typically involves pulling on the proximal end of the gastrostomy tube until the internal bolster fails and is drawn through the stoma. As can readily be appreciated, such a procedure can be quite painful to the patient and can result in damage to the stoma, thereby delaying when the replacement device can be implanted.

Another shortcoming of many low-profile replacement PEG devices is that such devices typically do not last as long as initially-implanted gastrostomy tube assemblies (most commonly due to failure of their internal anchoring mechanisms or due to clogging or other failure of their valve mechanisms) and, therefore, must be replaced more frequently than is the case with initially-implanted gastrostomy tube assemblies.

Still another shortcoming of many low-profile replacement PEG devices is that such devices are typically not adjustable in length. This can be problematic because there is often an appreciable variation in stoma length from patient to patient. Consequently, it is typically necessary, after removal of the initially-implanted tube and prior to implantation of the replacement device, to measure the length of the stoma and then to select a replacement device having an appropriate length. As can readily be appreciated, this approach requires that there be made available an inventory of replacement devices of varying lengths.

In order to avoid the aforementioned shortcomings of low-profile replacement PEG devices while, at the same time, avoiding the above-described problems associated with having a gastrostomy tube extend externally for a substantial length, there have recently been devised a number of adaptors designed for use in converting an initially-implanted gastrostomy tube into a low-profile PEG device. One such adaptor is disclosed in U.S. Pat. No. 5,549,657, inventors Stern et al., which issued Aug. 27, 1996, and which is incorporated herein by reference. According to said patent, an adaptor is disclosed therein that is designed for use with a gastostomy feeding tube which has been inserted by means of conventional endoscopic procedures and which has been cut to a desired length by a surgeon. The adaptor is said to comprise an anti-reflux valve assembly having a stem which can be plugged into the open end of the feeding tube. The valve assembly is said to contain a seal which functions as a one-way valve to prevent reflux of gastric contents but which permits the introduction of feeding solution into the feeding tube. A clamp is placed around the feeding tube and the valve stem and is locked into place to secure the valve assembly to the feeding tube at a location flush with the patient's skin. A silicone cover is placed around the clamp to protect the patient from skin irritation caused by the clamp and also to protect the clamp and valve assembly from contaminants.

Although the aforementioned adaptor favorably addresses some of the problems discussed above, the present inventors have identified certain shortcomings associated therewith. One such shortcoming is that the valve assembly of the subject adaptor relies upon the use of a silicone gasket having a Y-shaped slot through which a cannula is typically inserted to deliver food and/or medications. However, such a silicone gasket, after repeated insertions of the cannula therethrough, has a tendency to tear or to otherwise fail to act reliably as a one-way valve. Consequently, because the adaptor cannot easily be disconnected from the gastrostomy feeding tube once connected thereto, replacement of a worn adaptor requires the removal and replacement of the gastrostomy tube as well.

Another shortcoming with the aforementioned adaptor is that it possesses a relatively small lumen through which fluid may pass. In addition, due to its manner of operation, the valve tends to get clogged over time, further restricting fluid flow.

Still another shortcoming with the aforementioned adaptor is that the clamp of said adaptor has a tendency to pinch the proximal end of the gastrostomy tube at those points where the male and female sections of the clamp are joined. Such pinching, over time, has a tendency to cause the tube to tear.

SUMMARY OF THE INVENTION

It is an object of the present invention to provide a novel low profile adaptor designed for use with a medical catheter, such as a gastrostomy feeding tube.

It is another object of the present invention to provide a low profile adaptor as described above that overcomes at least some of the shortcomings discussed herein in connection with existing PEG devices, in general, and low profile PEG adaptors, in particular.

Therefore, according to one aspect of the invention, there is provided a low profile adaptor well-suited for use with a medical catheter, such as a gastrostomy feeding tube, the medical catheter having a proximal end, said low profile adaptor comprising (a) a first tube, said first tube being adapted for connection to the proximal end of the medical catheter for fluid communication therewith; (b) a generally tubular key, said generally tubular key having a first end and a second end, said first end being adapted for connection to an external tube for fluid communication therewith; and (c) a second tube, said second tube being switchable, only when unlocked by engagement with said second end of said generally tubular key, between an open position in which said second tube is in fluid communication with said first tube and a closed position in which said second tube is not in fluid communication with said first tube.

In a preferred embodiment, the low profile adaptor comprises a disc-shaped housing, the housing being provided with a bottom opening and a side slot, the side slot having a uniform width, except for an enlarged area at one end thereof. A tube is disposed within the housing, the tube having a first end, a second end, and a longitudinal bore. The first end is aligned with the bottom opening and is adapted to be inserted into the proximal end of a gastrostomy feeding tube. A ratchet-type clamp is disposed within the housing and is used to secure the gastrostomy feeding tube to the first end of the tube. A lateral slot is formed in the tube at its second end and is in fluid communication with the longitudinal bore. A dial is disposed within the housing and is rotatably mounted on the second end of the tube, the dial including a radial channel. When the outer end of the channel is aligned with the enlarged end of the side slot, the inner end of the channel is not in fluid communication with the lateral slot of the tube. When, however, the outer end of the channel is aligned with the opposite end of the slot, the inner end of the channel is in fluid communication with the lateral slot. Movement of the channel between these two positions is effected with an adaptor fitting. The adaptor fitting has a first end insertable into an external tube, such as a food delivery tube, and a second end insertable into and removable from the outer end of the channel only when the outer end of the channel is aligned with the enlarged end of the side slot.

According to another aspect of the invention, there is provided a low profile adaptor well-suited for use with a medical catheter, the medical catheter having a proximal end, said low profile adaptor comprising (a) a housing, said housing being provided with an opening and a slot, said opening being dimensioned to receive the proximal end of a medical catheter; (b) a first tube disposed within said housing, said first tube having a first end, a second end and a longitudinal bore, said first end being aligned with said opening and being adapted for connection to the proximal end of the medical catheter for fluid communication therewith, said second end having a lateral slot in fluid communication with said longitudinal bore; and (c) a second tube disposed within said housing, said second tube having a first end, a second end, and a longitudinal bore, said first end of said second tube being aligned with and positioned behind said slot and being adapted for connection to an external tube for fluid communication therewith, said second tube being movable between an open position in which said second end of said second tube is in fluid communication with said lateral slot of said first tube and a closed position in which said second end of said second tube is not in fluid communication with said lateral slot of said first tube.

According to yet another aspect of the invention, there is provided a low profile adaptor well-suited for use with a medical catheter, the medical catheter having a proximal end, said low profile adaptor comprising (a) a housing, said housing being provided with an opening and a slot, said opening being dimensioned to receive the proximal end of a medical catheter; (b) a first tube disposed within said housing, said first tube having a first end, a second end and a longitudinal bore, said first end being aligned with said opening and being adapted for connection to the proximal end of a medical catheter for fluid communication therewith, said second end having a lateral slot in fluid communication with said longitudinal bore; and (c) a dial rotatably mounted on said second end of said first tube, said dial being shaped to include a second tube, said second tube having a first end, a second end, and a longitudinal bore, said first end of said second tube being aligned with said slot and being adapted for connection to an external tube, said second tube being movable between an open position in which said second end of said second tube is in fluid communication with said lateral slot of said first tube and a closed position in which said second end of said second tube is not in fluid communication with said lateral slot of said first tube.

According to still yet another aspect of the invention, there is provided a low profile adaptor well-suited for use with a medical catheter, the medical catheter having a proximal end, said low profile adaptor comprising (a) a first tube, said first tube having a first end adapted for insertion into the proximal end of a medical catheter; (b) a second tube, said second tube having a first end and a second end, said first end being adapted for connection to the distal end of an external tube for fluid communication therewith, said second end being switchable between an open position in which said second tube is in fluid communication with said first tube and a closed position in which said second tube is not in fluid communication with said first tube; and (c) a clamp adapted to be tightened around said first end of said first tube and the proximal end of a medical catheter inserted therebetween.

According to a further aspect of the invention, there is provided a low profile adaptor well-suited for use with a medical catheter, the medical catheter having a proximal end, said low profile adaptor comprising (a) a tube, said tube having a first end adapted for insertion into the proximal end of a medical catheter; and (b) a clamp adapted to be tightened around said first end of said tube and the proximal end of a medical catheter inserted therebetween, said clamp comprising a pair of identical clamp halves fitted together in a ratchet-type manner to jointly define a quasi-circular opening through which said first end of said tube and the proximal end of the medical catheter may be inserted.

According to still a further aspect of the invention, there is provided an adaptor well-suited for use with a medical catheter, the medical catheter having a proximal end, said low profile adaptor comprising (a) a tube, said tube having a first end adapted for insertion into the proximal end of a medical catheter; and (b) a resilient member insertable over said tube and engageable therewith for securing to said tube the proximal end of a medical catheter inserted therebetween.

As can readily be appreciated, although the adaptors discussed above are described as being low profile adaptors, such adaptors are also suitable for use with medical catheters, such as gastrostomy feeding tubes, that extend externally for several inches. Accordingly, the adaptors of the present invention are not limited to being low profile adaptors.

The present invention is also directed to a PEG device comprising a gastrostomy feeding tube having a proximal end and a distal end, an internal bolster secured to the distal end of the gastrostomy feeding tube, and an adaptor of the type described above secured to the proximal end of the gastrostomy feeding tube.

For purposes of the present specification and claims, relational terms like "top," "bottom," "upper," and "lower" are used to describe the present invention in a context in which the invention is secured to a catheter extending upwardly out of a patient. It is to be understood that, by orienting a patient such that the catheter extending outwardly in a direction other than upwardly, the directionality of the invention will need to be adjusted accordingly.

Additional objects, features, aspects and advantages of the present invention will be set forth, in part, in the description which follows and, in part, will be obvious from the description or may be learned by practice of the invention. In the description, reference is made to the accompanying drawings which form a part thereof and in which is shown by way of illustration specific embodiments for practicing the invention. These embodiments will be described in sufficient detail to enable those skilled in the art to practice the invention, and it is to be understood that other embodiments may be utilized and that structural changes may be made without departing from the scope of the invention. The following detailed description is, therefore, not to be taken in a limiting sense, and the scope of the present invention is best defined by the appended claims.

BRIEF DESCRIPTION OF THE DRAWINGS

The accompanying drawings, which are hereby incorporated into and constitute a part of this specification, illustrate preferred embodiments of the invention and, together with the description, serve to explain the principles of the invention. In the drawings wherein like reference numerals represent like parts.

DETAILED DESCRIPTION OF PREFERRED EMBODIMENTS

Figure 1:
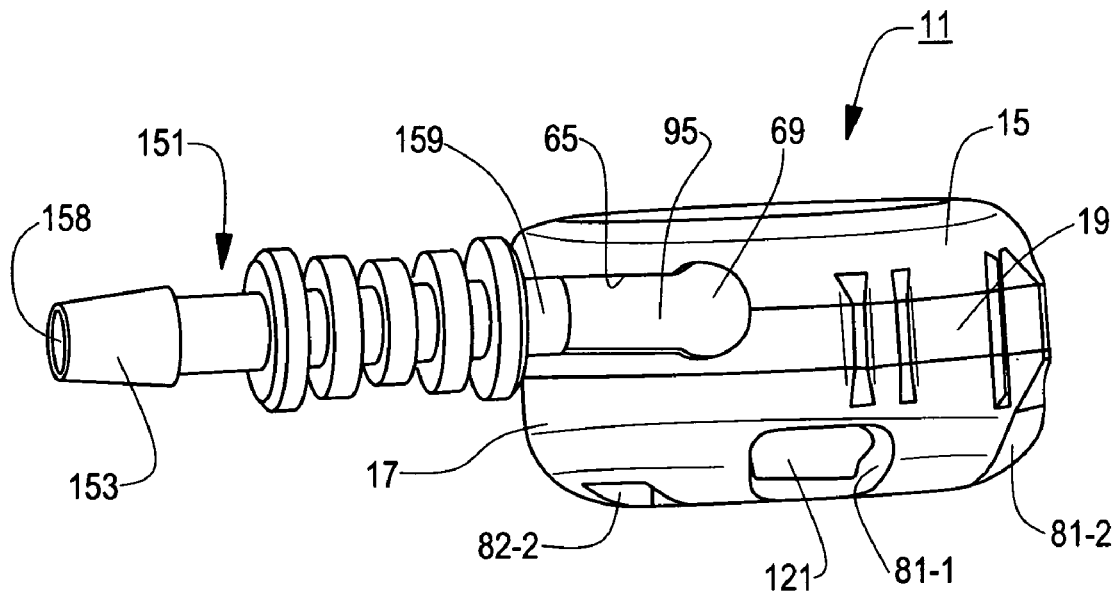
FIG. 1 is a top perspective view of a first embodiment of a low profile adaptor constructed according to the teachings of the present invention for use with a medical catheter, such as a gastrostomy feeding tube, said low profile adaptor being shown in its open position.
Figure 2:
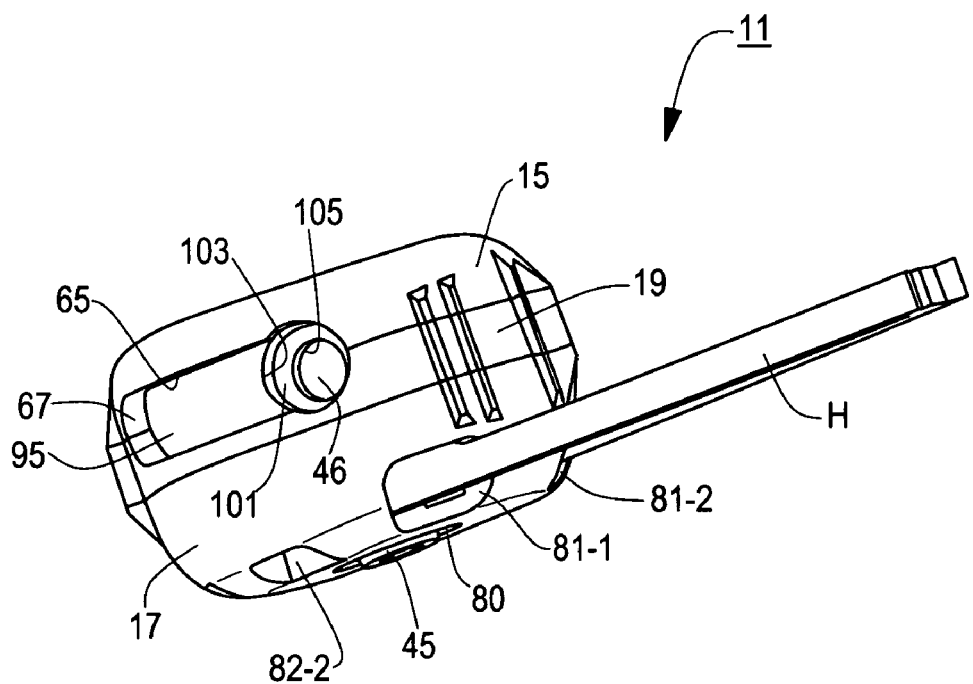
FIG. 2 is a bottom perspective view of the low profile adaptor of FIG. 1, said low profile adaptor being shown in its closed position with the adaptor fitting thereof not being shown and with a hemostat inserted into said low profile adaptor for tightening the clamp thereof.
Figure 3:
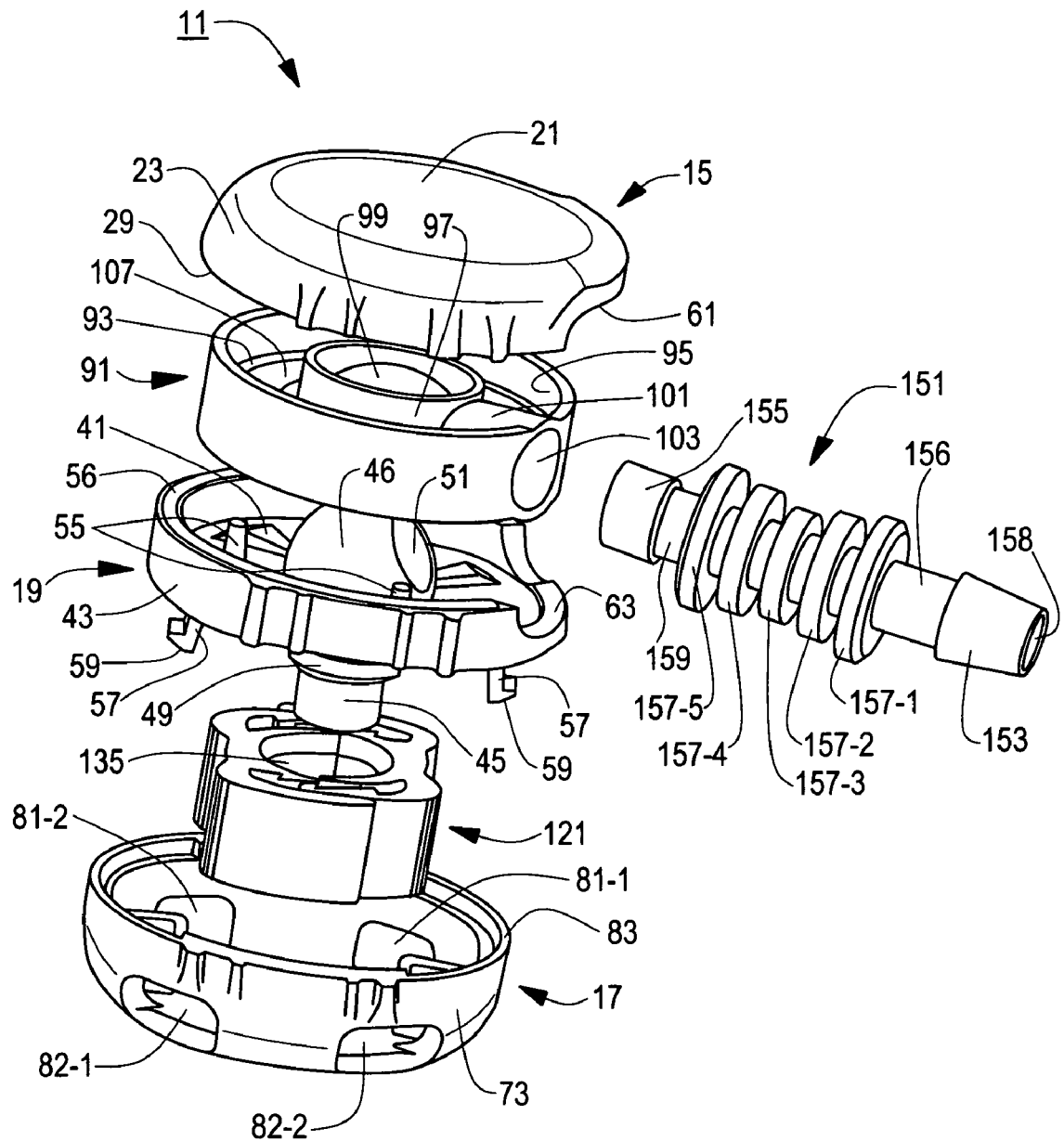
FIG. 3 is an exploded top perspective view of the low profile adaptor of FIG. 1.
Figure 4:
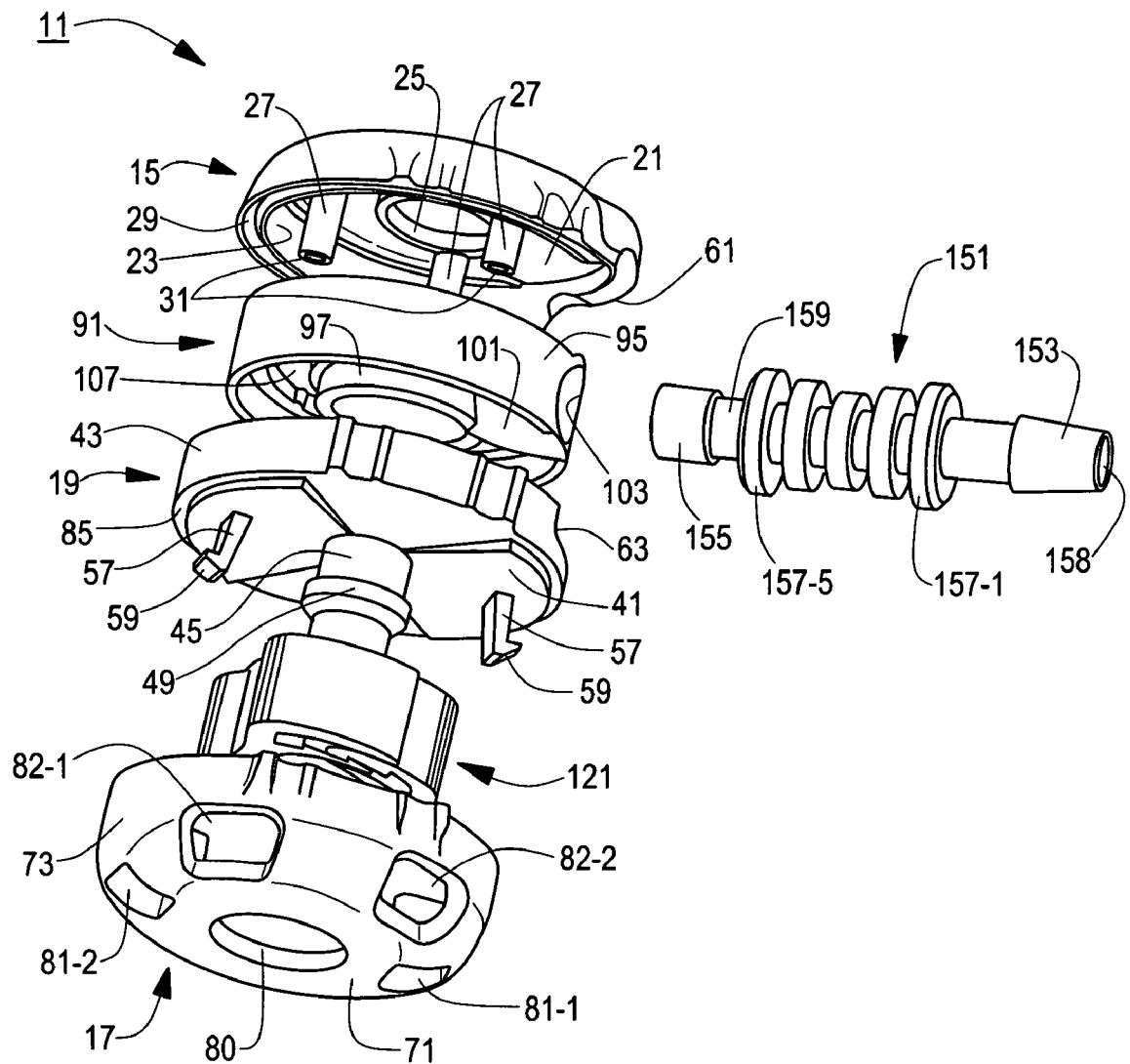
FIG. 4 is an exploded bottom perspective view of the low profile adaptor of FIG. 1.
Figure 5:
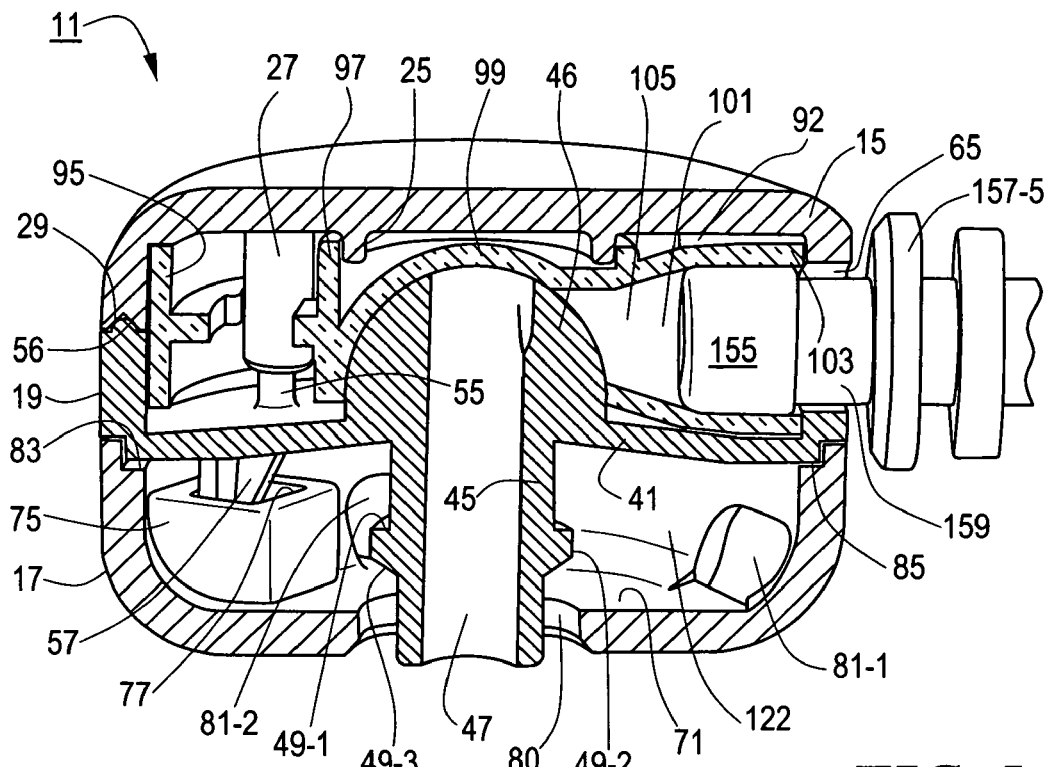
FIG. 5 is a top perspective view, partly in section, of the low profile adaptor of FIG. 1, said low profile adaptor being shown in its closed position with the clamp not being shown.
Figure 6:
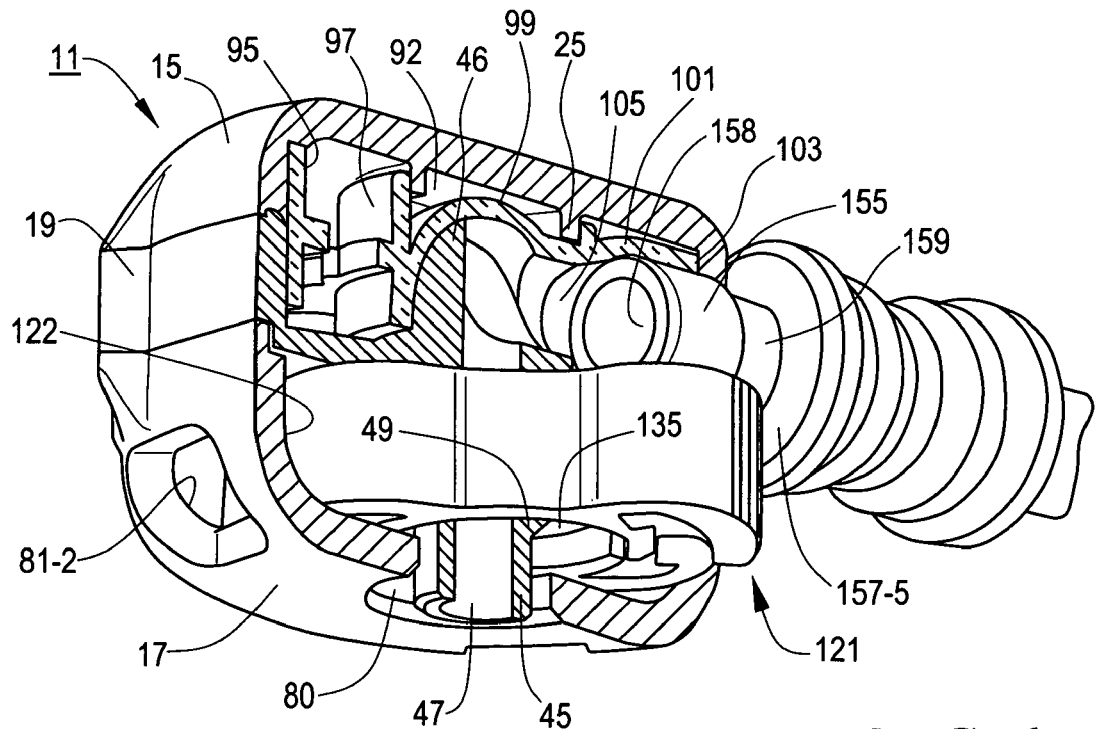
FIG. 6 is a bottom perspective view, partly in section, of the low profile adaptor of FIG. 1, said low profile adaptor being shown in its open position.

Referring now to FIGS. 1 through 6, there are shown various views of a first embodiment of a low profile adaptor constructed according to the teachings of the present invention for use with a medical catheter, such as a gastrostomy feeding tube, said low profile adaptor being represented generally by reference numeral 11.

Adaptor 11 comprises an upper housing member 15, a lower housing member 17 and an intermediate housing member 19, the collection of which define a generally disk-shaped housing.

Upper housing member 15 is shaped to include a generally circular top wall 21, a side wall 23 extending downwardly a short distance from the perimeter of top wall 21, and an open bottom. A circular ridge 25, the function of which will become apparent below, is formed on the bottom surface of top wall 21, ridge 25 being positioned concentrically around the center of top wall 21 and extending downwardly a short distance therefrom. Three posts 27, the function of which will also become apparent below, are also formed on the bottom surface of top wall 21, posts 27 being equidistantly positioned around ridge 25 between ridge 25 and side wall 23 and extending downwardly from top wall 21 a short distance beyond the bottom edge 29 of side wall 23. For reasons to become apparent below, each post 27 is provided with an opening 31 at its bottom end. The outer surface of side wall 23 is contoured to facilitate its being handled by an operator.

Figure 7:
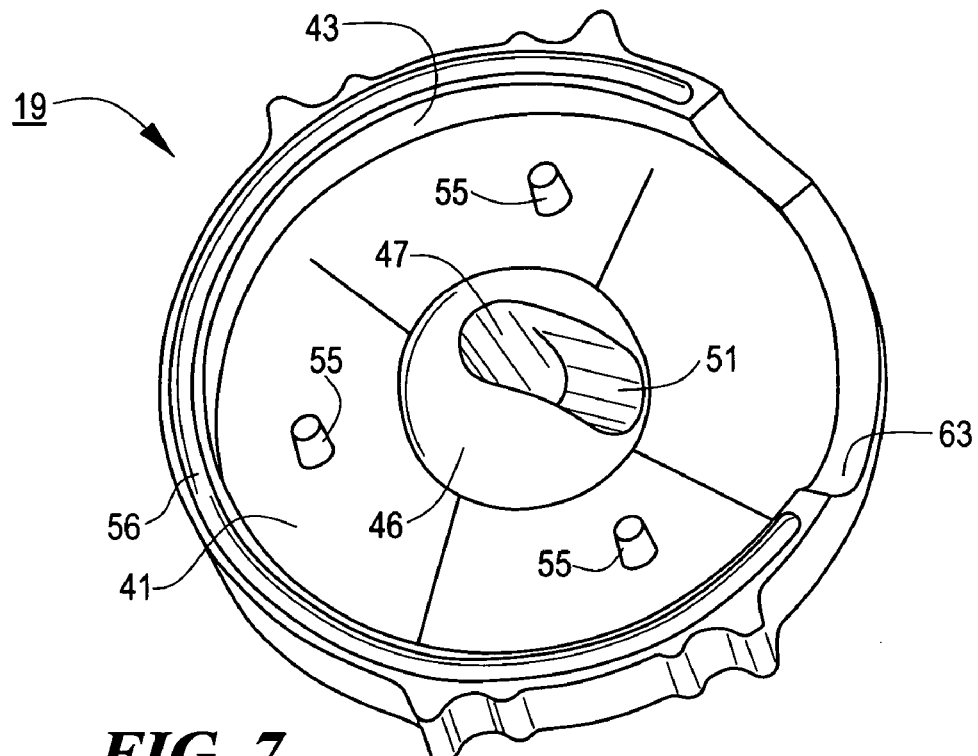
FIG. 7 is a top perspective view of the intermediate housing member shown in FIG. 1.

Intermediate housing member 19, which is also shown separately in FIG. 7, is shaped to include a generally circular bottom wall 41, a side wall 43 extending upwardly a short distance from the perimeter of bottom wall 41, and an open top. A generally mushroom-shaped tube 45 having a longitudinal bore 47 is formed at the center of bottom wall 41 and extends transversely upwardly and downwardly away from bottom wall 41. The lower portion of tube 45 is generally cylindrical and is shaped to include a circumferential outer flange 49. Flange 49, the function of which will become apparent below, is shaped to have a horizontal top surface 49-1, a vertical side surface 49-2, and a sloped bottom surface 49-3. The upper portion 46 of tube 45 is generally dome-shaped and is shaped to include a lateral slot 51, slot 51 being in fluid communication with bore 47 for reasons to become apparent below.

Intermediate housing member 19 is also shaped to include three pegs 55 formed on the top surface of bottom wall 41 and extending upwardly a short distance therefrom. The top ends of pegs 55 are inserted into posts 27 and are secured thereto by an interference fit. For reasons to become apparent below, intermediate housing member 19 is further shaped to include a pair of resilient legs 57 formed on the bottom surface of bottom wall 41 and extending downwardly a short distance therefrom, each leg 57 terminating at its bottom end in an outwardly extending foot 59.

Side wall 43 of member 19, which has a diameter matching that of side wall 23 of member 15 and which is similarly contoured on its outer surface for ease of handling, has a top edge 56 that is shaped complementarily to bottom edge 29 of wall 23 so that side wall 43 of intermediate housing member 19 and side wall 23 of upper housing member 15 fit together. (Preferably, an adhesive, not shown, is also applied between edges 29 and 56 to fixedly secure housing member 19 and housing member 15 to one another.) Side wall 23 of upper housing member 15 and side wall 43 of intermediate housing member 19 are provided with complementary recessed areas 61 and 63, respectively, that collectively define a slot 65 having a pair of ends 67 and 69. For reasons to become apparent below, end 67 is aligned with lateral slot 51, and slot 65 is uniform in width, except at end 69, which is enlarged relative to the remainder of slot 65.

Figure 8:
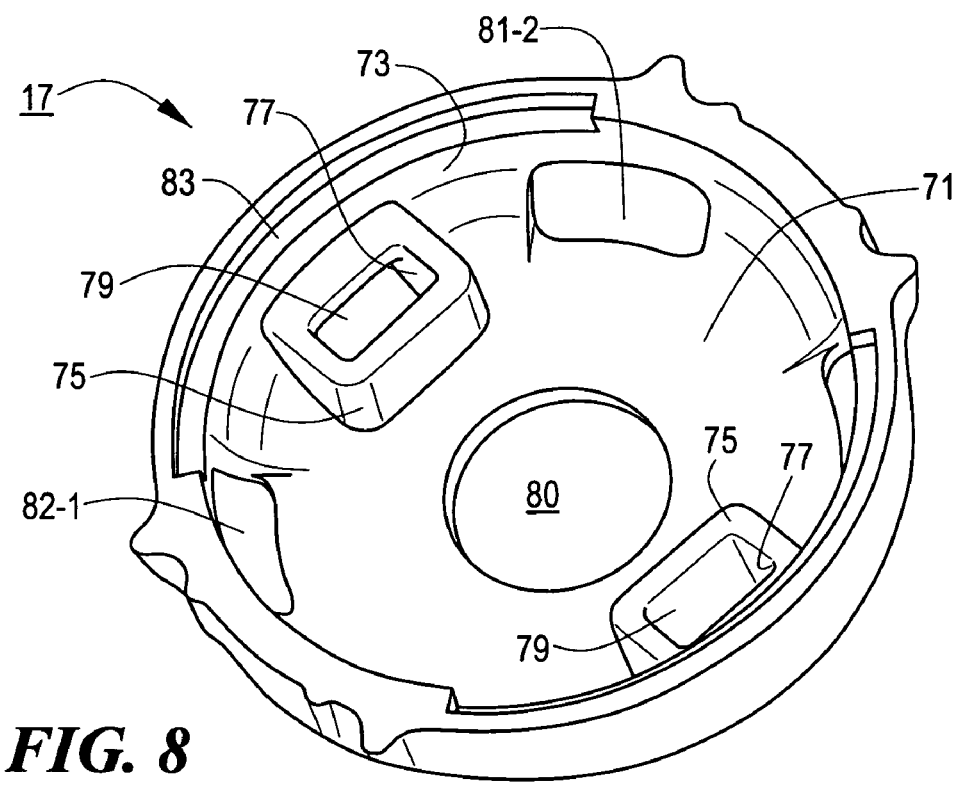
FIG. 8 is a top perspective view of the lower housing member shown in FIG. 1.
Figure 9:
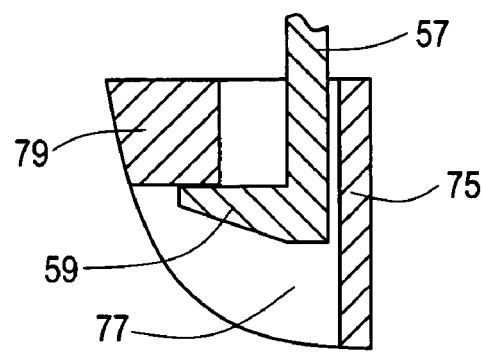
FIG. 9 is a fragmentary section view showing how the bottom portion of the leg of the intermediate housing member is securely retained within the post of the lower housing member.

Lower housing member 17, which is shown separately in FIG. 8, is shaped to include a circular bottom wall 71, a side wall 73 extending upwardly a short distance from bottom wall 71, and an open top. A pair of rectangular posts 75 are formed on the top surface of bottom wall 71 and extend upwardly a short distance therefrom. A cavity 77 extends longitudinally through each post 75, cavity 77 being sized and shaped to receive the bottom portion of one leg 57. A flange 79 is formed on the inside surface of post 75 and extends into cavity 77 so as to securely retain foot 59 within cavity 77 (see FIG. 9).

Lower housing member 17 is also shaped to include a central opening 80 provided in bottom wall 71, a first pair of openings 81-1 and 81-2 provided in side wall 73, and a second pair of openings 82-1 and 82-2 provided in side wall 73, the purpose of openings 80, 81-1, 81-2, 82-1 and 82-2 to become apparent below. Side wall 73 of member 17, which has a diameter matching that of side wall 43 of member 19 and which is similarly contoured on its outer surface for ease of handling, has a top edge 83 that is shaped complementarily to bottom edge 85 of wall 43 so that side wall 43 of intermediate housing member 19 and side wall 73 of lower housing member 17 fit together. (Preferably, an adhesive, not shown, is also applied between edges 83 and 85 to fixedly secure housing member 19 and housing member 17 to one another.)

Figure 10:
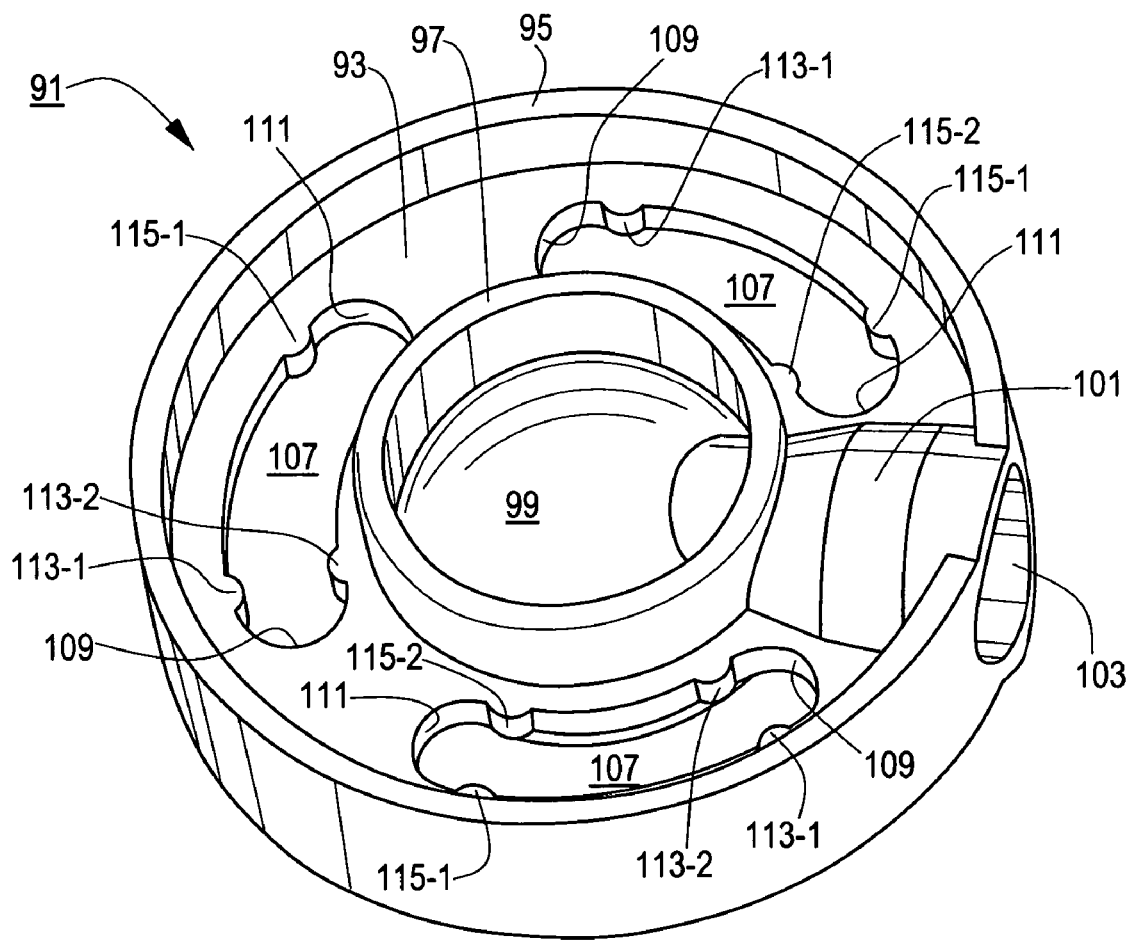
FIG. 10 is a top perspective view of the dial shown in FIG. 1.

Adaptor 11 also comprises a dial 91, dial 91 being disposed within an upper chamber 92 jointly defined by upper housing member 15 and intermediate housing member 19. Dial 91, which is shown separately in FIG. 10, is a generally disc-shaped member comprising a generally circular wall 93, an outer side wall 95 surrounding the perimeter of wall 93 and extending upwardly and downwardly a short distance therefrom, and an inner side wall 97 concentrically spaced inwardly from outer side wall 95 and extending upwardly and downwardly a short distance from circular wall 93. That portion of wall 93 circumscribed by inner wall 97 is in the shape of a dome 99, dome 99 being rotatably mounted on dome-shaped top portion 46 of tube 45, with inner side wall 97 being retained between ridge 25 and posts 27.

A tubular channel 101 having an outer end 103 of comparatively greater diameter and an inner end 105 of comparatively lesser diameter is formed in dial 91 and extends radially through outer side wall 95 and inner side wall 97. For reasons to become apparent below, dial 91 is oriented within chamber 92 so that channel 101 is aligned with slot 65, with outer end 103 of channel 101 having a size and shape that substantially matches that of enlarged end 69 of slot 65.

Three arcuate slots 107 are provided in wall 93, each slot 107 receiving a post 27 therethrough. Slots 107 are appropriately dimensioned and formed within wall 93 so that, when channel 101 is aligned with enlarged end 69 of slot 65, each post 27 is positioned at a first end 109 of its corresponding slot 107 whereas when channel 101 is aligned with end 67 of slot, each post 27 is positioned at a second end 111 of its corresponding slot 107. A first pair of detents 113-1 and 113-2 extend into each slot 107 proximate to its first end 109, and a second pair of detents 115-1 and 115-2 extend into each slot 107 proximate to its second end 111. Detents 113 and 115 serve to provide an operator with tactile and audible indicators that posts 27 have reached ends 109 and 111, respectively, and also serve to retain posts 27 at ends 109 and 111, respectively, until otherwise desired.

Figure 12:
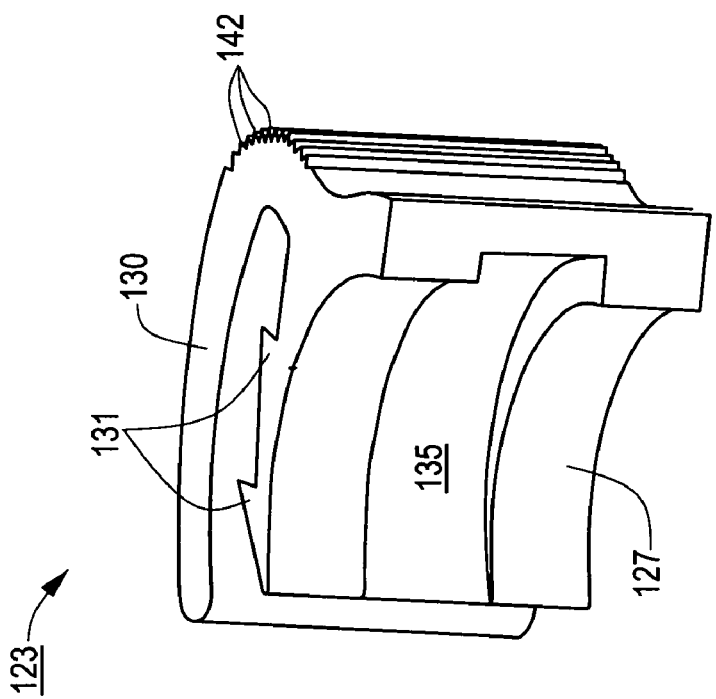
FIG. 12 is a fragmentary perspective view of one of the two clamp halves shown in FIG. 11.
Figure 11:
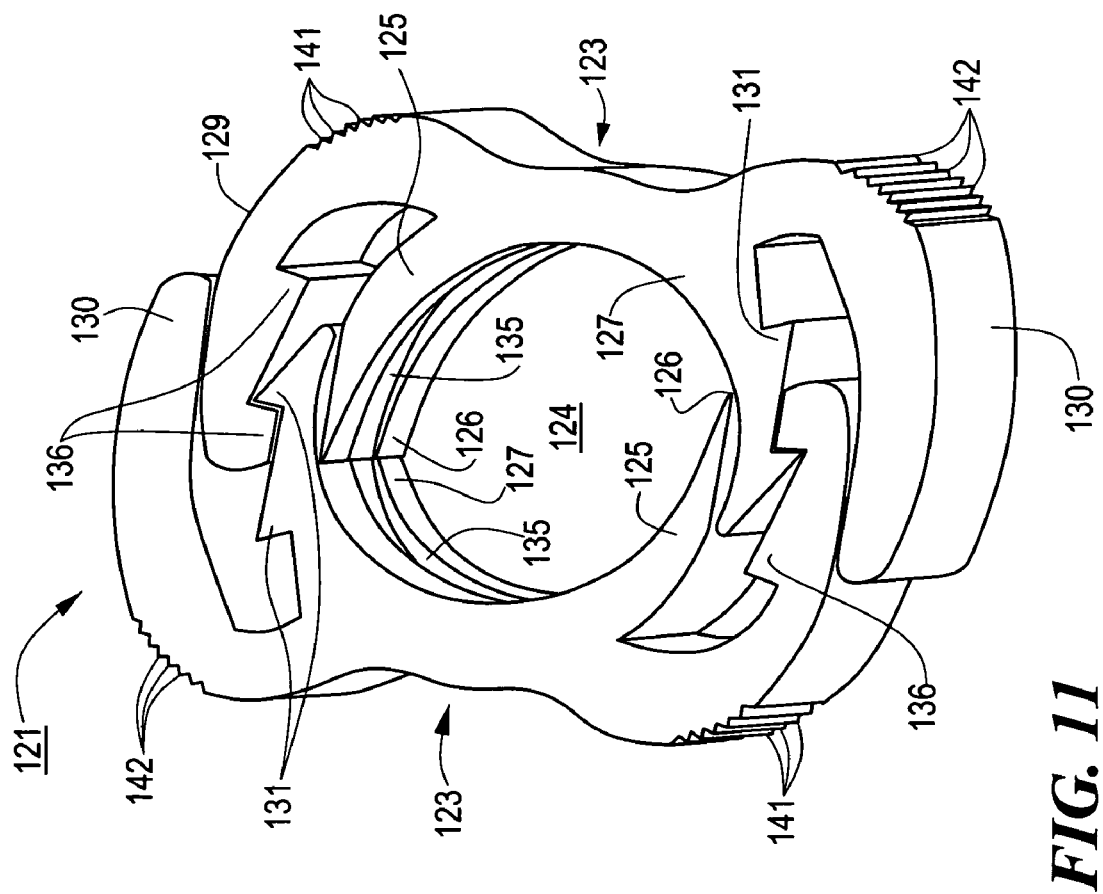
FIG. 11 is a top perspective view of the clamp shown in FIG. 1.

Adaptor 11 additionally comprises a clamp 121 for securing the proximal end of a gastrostomy tube onto the lower portion of tube 45, clamp 121 being disposed within a lower chamber 122 jointly defined by lower housing member 17 and intermediate housing member 19. Clamp 121, which is shown separately in FIGS. 11 and 12, comprises a pair of identical clamp halves 123 that are fitted together to jointly define a quasi-circular opening 124 through which the lower portion of tube 45 is inserted. Each clamp half 123 comprises a pair of curved inner legs 125 and 127 and a pair of curved outer legs 129 and 130.

A generally rectangular longitudinal groove 135 is continuously provided along the inside surfaces of legs 125 and 127, groove 135 being sized and shaped to receive flange 49 of tube 45 therewithin so that the proximal end of a gastrostomy feeding tube inserted over flange 49 may be securely retained thereon by clamp 121. The outer end 126 of leg 125 is bent slightly outwardly so as to minimize any pinching of a gastrostomy tube between halves 123, particularly during tightening of clamp 121. The outside surface of leg 127 is shaped to define a set of teeth 131, and the inside surface of leg 129 is shaped to define a complementary set of teeth 136 so that the pair of clamp halves 123 may be tightened together in a ratchet-type manner. Such tightening is preferably performed by inserting a hemostat H or similar device into openings 81 (see FIG. 2), gripping leg 129 of one clamp half 123 and leg 130 of the other clamp half 123 with hemostat H and using hemostat H to slide leg 129 across leg 127. Hemostat H is then removed from openings 81 and inserted into openings 82, with the above procedure being repeated. To facilitate the gripping of clamp 121 with a hemostat or the like, the outer surfaces of legs 129 and 130 are provided with a number of transverse ridges 141 and 142, respectively.

It is to be understood that clamp 121 could be modified so as to have a hinge at one end thereof and a ratchet-type arrangement at the other end thereof, instead of having a ratchet-type arrangement at both ends thereof as in the present embodiment. In addition, other arrangements for fastening the gastrostomy feeding tube to tube 45, as will be exemplified below, are similarly contemplated as falling with the scope of the present invention.

Adaptor 11 further comprises an adaptor fitting 151, adaptor fitting 151 being a generally tubular unitary member shaped to include a proximal end 153, a distal end 155, an intermediate length 156 shaped to include a plurality of transverse rings 157-1 through 157-5, and a longitudinal bore 158. Proximal end 153, which is barb-shaped, is adapted for insertion into the distal end of an external tube, such as a food and/or medication delivery tube. Distal end 155, which is cylindrically-shaped and which has an outer diameter slightly larger than a waist portion 159 of intermediate length 156 located distal to ring 157-5, is sized for insertion through end 69 of slot 65 and into channel 101 in such a way as to frictionally engage channel 101. Distal end 155 also has a diameter greater than the width of slot 65 (except at end 69), with waist 159 having a diameter less than the width of slot 65.

Consequently, to rotate dial 91 so that channel 101 is moved from a closed position in which it is aligned with end 69 of slot 65 but is not aligned with lateral slot 51 of tube 45 to an open position in which it is aligned with both end 67 of slot 65 and lateral slot 51 of tube 45, one must first insert distal end 155 of fitting 151 through end 69 of slot 65 and into channel 101 until engaged therewith. With distal end 155 thus engaged with channel 101, fitting 151 and dial 91 can then be rotated relative to tube 45 from said closed position to said open position, thereby enabling fluid to be conducted from fitting 151 through tube 45 and into a gastrostomy feeding tube connected to tube 45. (In view of the above, it can be seen that fitting 151 functions much like a key that permits the switching of dial 91 from a closed position to an open position.) When feeding has been completed, fitting 151 and dial 91 are rotated from said open position to said closed position, and fitting 151 is preferably then removed from channel 101 to prevent any unintended switching.

As can be appreciated, because distal end 155 is greater in diameter than slot 65, except at end 69, fitting 151 cannot be removed from channel 101 when dial 91 is in said open position, i.e., during feeding. Moreover, because dial 91 cannot readily be switched from a closed position to an open position without the use of fitting 151, adaptor 11 also works well at preventing reflux of gastric fluids between feedings.

Rings 157 facilitate handling of adaptor fitting 151, with ring 157-1 additionally serving as a stop for the distal end of a food or medication delivery tube inserted over proximal end 153 and with ring 157-5 additionally serving as a stop to prevent continued insertion of fitting 151 into channel 101.

Figure 13:
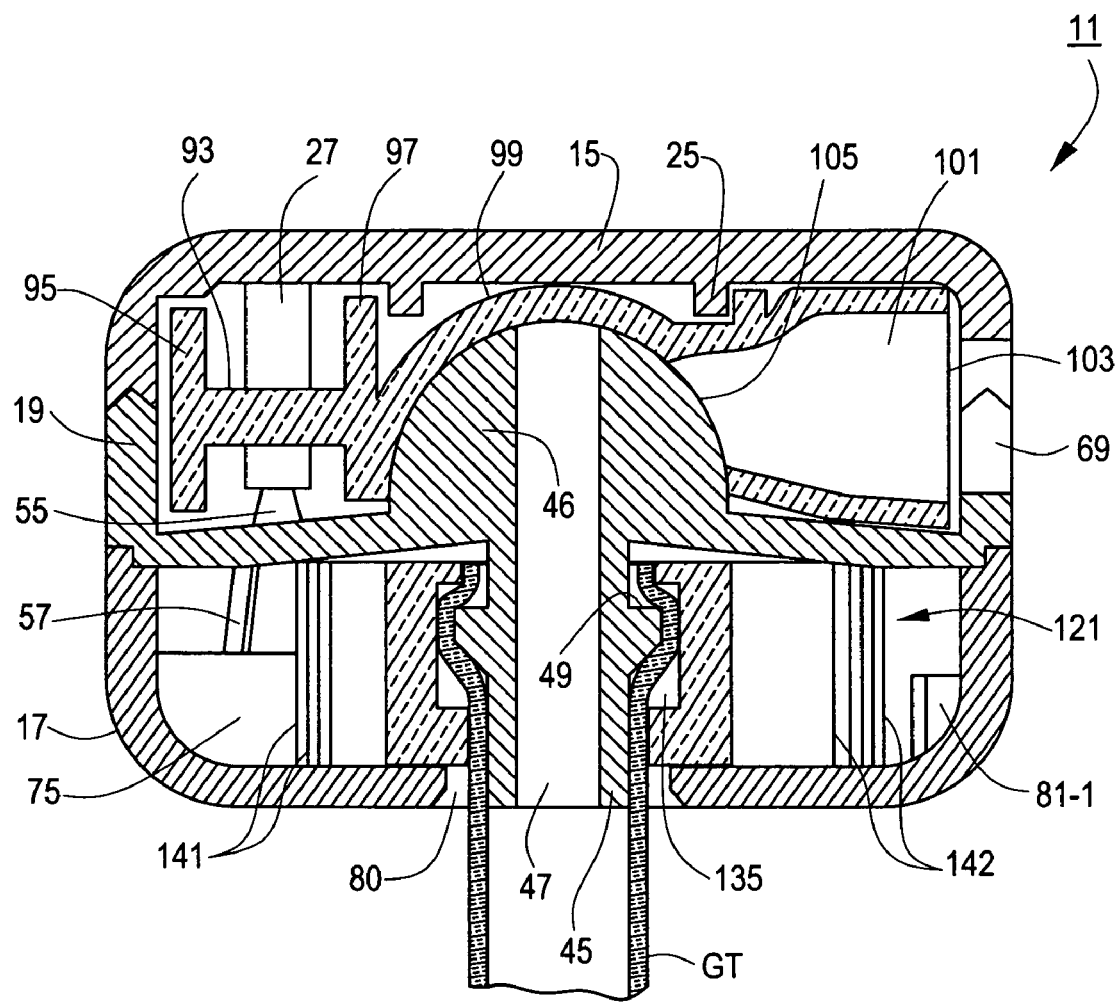
FIG. 13 is a section view of the low profile adaptor of FIG. 1 connected to a gastrostomy feeding tube, said low profile adaptor being shown in its closed position with its adaptor fitting removed therefrom.

In use, a gastrostomy feeding tube is implanted in a patient by a physician in the manner described above so that the distal end of the tube is positioned in the patient's stomach and retained therein using an internal bolster, with the proximal end of the tube extending externally for a distance of several inches. The physician (or other medical care giver) then cuts the implanted gastrostomy feeding tube to a desired length. With channel 101 switched to the closed position and with fitting 151 preferably removed from channel 101, the physician then inserts the proximal end of the implanted gastrostomy feeding tube up through opening 80 of adaptor 11 and completely over flange 49 of tube 45. (Bottom surface 49-3 of flange 49 is sloped to facilitate the sliding of the proximal end of the gastrostomy feeding tube up over flange 49.) The physician then uses a hemostat or similar device in the manner described above to close clamp 121 around the proximal end of the gastrostomy feeding tube so that the gastrostomy feeding tube is securely fixed to tube 45. Attachment of adaptor 11 to the gastrostomy feeding tube is now complete. (It may be noted that adaptor 301 has a retentive force, or grip strength, on tube GT of at least approximately 17 pounds.) As can be seen in FIG. 13, adaptor 11, in the aforementioned closed state, serves to prevent reflux of gastric fluids conveyed by gastrostomy feeding tube GT.

Figure 14:
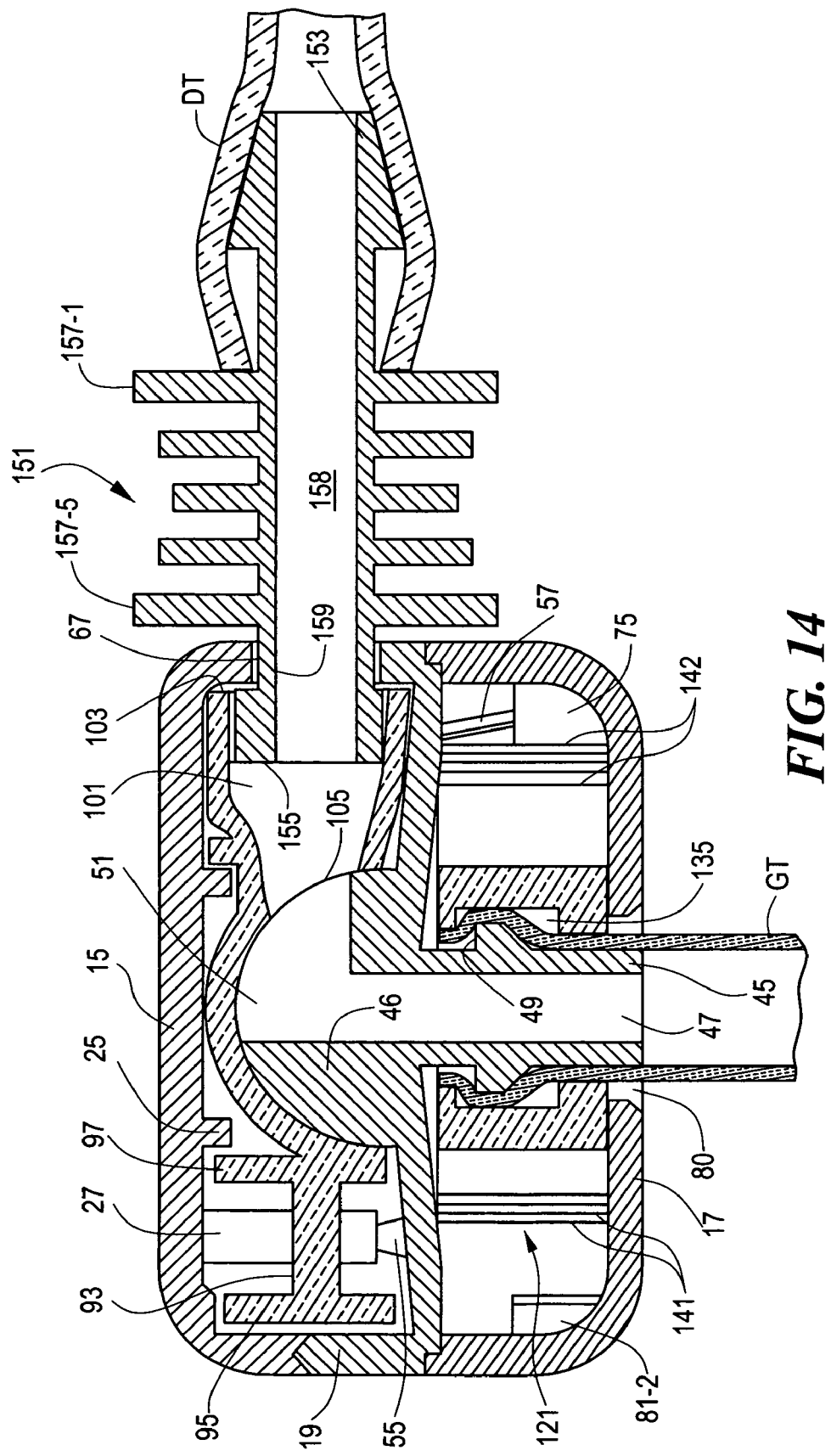
FIG. 14 is a section view of the low profile adaptor of FIG. 1 connected to a gastrostomy feeding tube, said low profile adaptor being shown in its open position with a food and/or medication delivery tube connected thereto.

Referring now to FIG. 14, when the administering of food and/or medications to the patient is desired, a delivery tube DT is secured to proximal end 153 of adaptor fitting 151, distal end 155 of adaptor fitting 151 is inserted into channel 101, and channel 101 is then switched from its closed position to its open position. With channel 101 thus switched to its open position, food and/or medications are permitted to flow from delivery tube DT to gastrostomy feeding tube GT via longitudinal bore 158 of adaptor fitting 151, channel 101, lateral slot 51 of tube 45 and longitudinal bore 47 of tube 45, respectively. Also, as noted previously, because of the relative sizes of distal end 155 and end 67 of slot 65, distal end 155 cannot be removed from channel 101 while channel 101 is switched to the open position.

Figure 15:
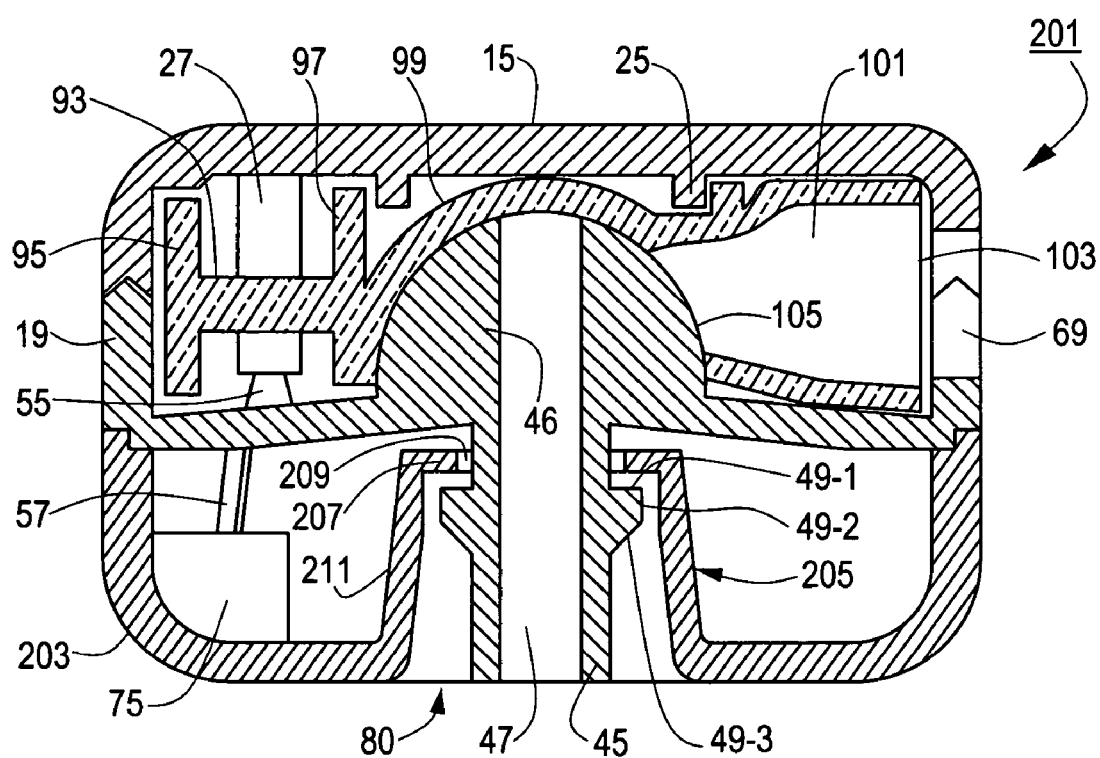
FIG. 15 is a section view of a second embodiment of a low profile adaptor constructed according to the teachings of the present invention for use with a medical catheter, such as a gastrostomy feeding tube, said low profile adaptor being shown in its closed position with the adaptor fitting not being shown.

Referring now to FIG. 15, there is shown a section view of a second embodiment of a low profile adaptor constructed according to the teachings of the present invention for use with a medical catheter, such as a gastrostomy feeding tube, said low profile adaptor being represented generally by reference numeral 201.

Adaptor 201 is similar in many respects to adaptor 11, the principal differences between the two adaptors being (i) that lower housing member 17 of adaptor 11 is replaced with lower housing member 203 in adaptor 201 and (ii) that adaptor 201 does not include clamp 121.

Lower housing member 203 is similar in many respects to lower housing member 17, the principal differences between the two lower housing members being (i) that lower housing member 203 does not include openings 81-1, 81-2, 82-1 and 82-2 and (ii) that lower housing member 203 is shaped to further include a sleeve 205 extending upwardly from opening 80.

Sleeve 205, which is a resilient member capable of flexing outwardly about its bottom end in the manner to be discussed below, terminates at its top end in an inwardly-directed circumferential flange 207, flange 207 defining an opening 209 through which tube 45 of intermediate housing member 19 extends. Sleeve 205 is appropriately dimensioned so that flange 207 is positioned just above top surface 49-1 of flange 49 and side wall 211 of sleeve 205 is positioned just outside side surface 49-2 of flange. In this manner, as will be seen below, sleeve 205 may be used to securely clamp a gastrostomy feeding tube to flange 49.

Figure 16:
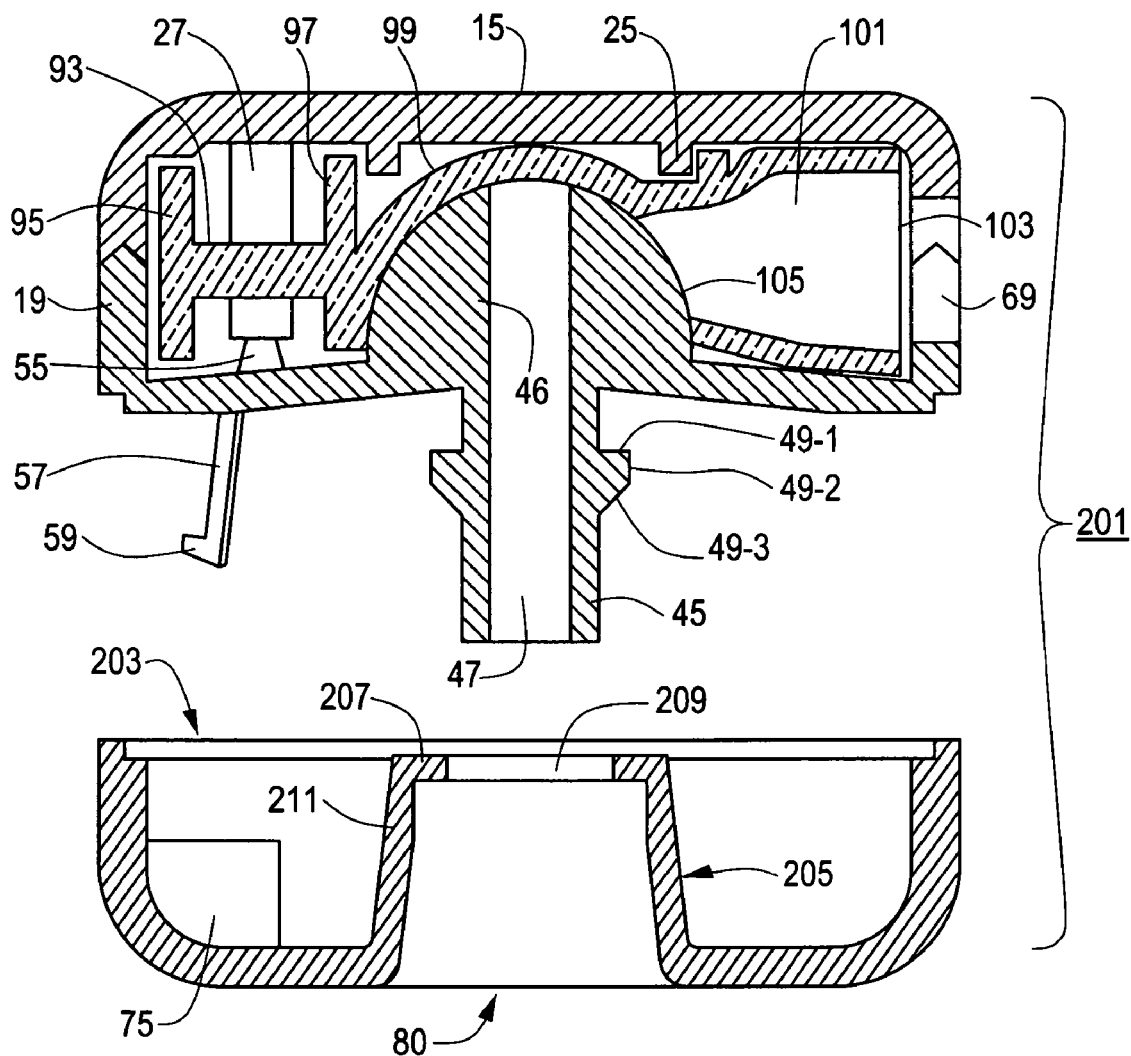
FIG. 16 is a section view of the low profile adaptor of FIG. 15, prior to attachment of the lower housing member to the intermediate housing member and with the adaptor fitting not being shown.
Figure 17:
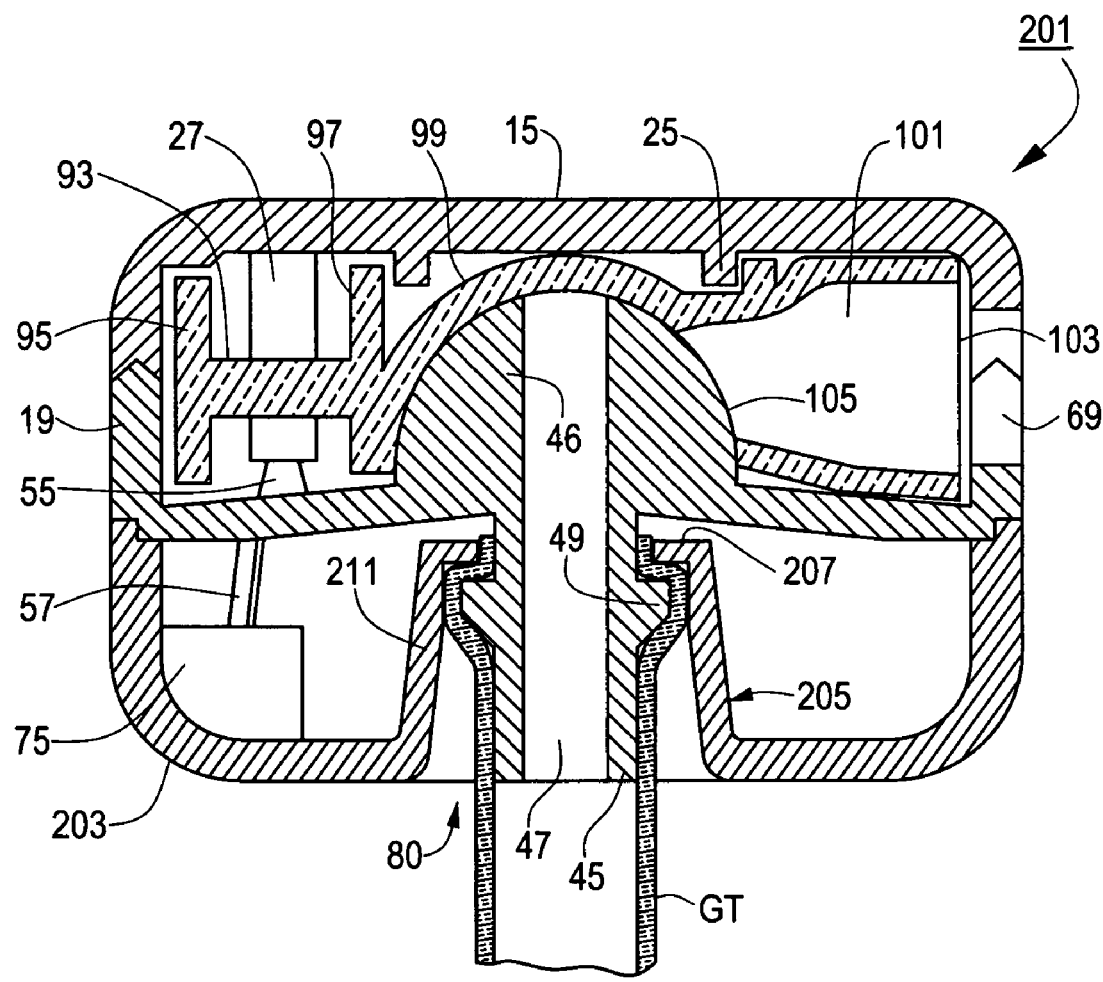
FIG. 17 is a section view of the low profile adaptor of FIG. 15 connected to a gastrostomy feeding tube, said low profile adaptor being shown in its closed position with the adaptor fitting not being shown.

Referring now to FIG. 16, there is shown a section view of adaptor 201, prior to the attachment of lower housing member 203 to intermediate housing member 19. With adaptor 201 initially in this unassembled state, one may install adaptor 201 on a patient as follows: First, the proximal end of an implanted gastrostomy feeding tube is inserted up through opening 80, sleeve 205 and opening 209, respectively, of lower housing 203. The gastrostomy feeding tube is then cut to a suitable length for low profile usage. Next, the proximal end of the gastrostomy feeding tube is inserted up over flange 49 of tube 45. Next, sleeve 205 of lower housing member 203 is passed up over tube 45 and that portion of the gastrostomy feeding tube that has been inserted thereover while, at the same time, foot 59 is inserted into post 75. As flange 207 is advanced over that portion of the gastrostomy feeding tube overlying sloping surface 49-3 of flange 49, surface 49-3 (as well as that portion of gastrostomy feeding tube overlying surface 49-3) forces sleeve 205 to flex outwardly for clearance. Such flexion of sleeve 205 continues until flange 207 has been advanced completely past surface 49-2 of flange 49. Once flange 207 has completely cleared surface 49-2 of flange 49 (as well as that portion of gastrostromy feeding tube overlying surface 49-2), sleeve 205 springs back to its preflexed state, clamping the gastrostomy feeding tube against flange 49 (see FIG. 17). Thus installed, adaptor 201 may be used in the same manner as adaptor 11. It may be noted that adaptor 201 has a retentive force, or grip strength, on tube GT of at least approximately 17 pounds.

It may also be noted that the step of bringing together lower housing member 203 and intermediate housing member 19 may be performed using only one hand, for example, by gripping the bottom surface of lower housing member 203 with the forefinger and the middle finger of one hand positioned on opposite sides of the gastrostomy feeding tube, by gripping the top surface of upper housing member 15 with the thumb of the same hand and then by bringing together the two portions using the foregoing three fingers.

As can be appreciated, one distinction between adaptor 201 and adaptor 11 is that adaptor 201 does not require the use of a hemostat or other external instrument for securing the gastrostomy feeding tube to tube 45.

Figure 18:
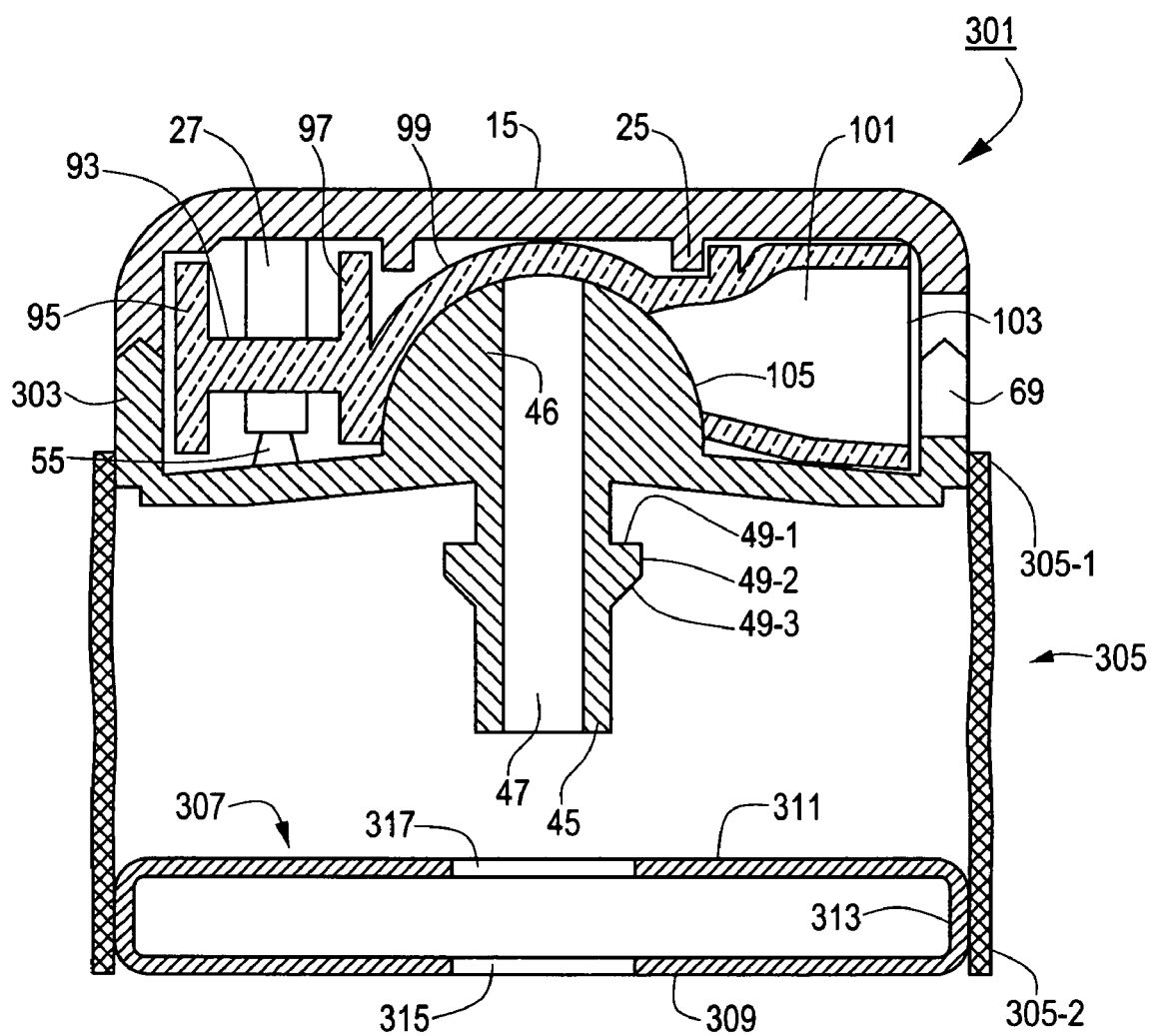
FIG. 18 is a section view of a third embodiment of a low profile adaptor constructed according to the teachings of the present invention for use with a medical catheter, such as a gastrostomy feeding tube, said low profile adaptor being shown in its closed position with the adaptor fitting not being shown, said low profile adaptor also being shown in an expanded state prior to the engagement of the tube flange by the annular snap.

Referring now to FIG. 18, there is shown a section view of a third embodiment of a low profile adaptor constructed according to the teachings of the present invention for use with a medical catheter, such as a gastrostomy feeding tube, said low profile adaptor being represented generally by reference numeral 301.

Adaptor 301 is similar in many respects to adaptor 201, the principal differences between the two adaptors being (i) that intermediate housing member 19 of adaptor 201 is replaced with intermediate housing member 303 in adaptor 301 and (ii) that lower housing member 203 of adaptor 201 is replaced with the combination of a length of longitudinally compressible tubing 305 and an annular snap 307.

Intermediate housing member 303 is identical to intermediate housing member 19, except that intermediate housing member 303 does not include legs 57.

Tubing 305, which is preferably made of an elastomeric material, such as silicone rubber, is fixed at a first end 305-1 to intermediate housing 303 and is fixed at a second end 305-2 to annular snap 307. The securing of tubing 305 to each of intermediate housing 303 and snap 307 may be achieved with the aid of an adhesive, by overmolding ends 305-1 and 305-2 of tubing 305 onto housing 303 and snap 307, respectively, by the threaded engagement of ends 305-1 and 305-2 of tubing 305 to each of housing 303 and snap 307, respectively, or by other suitable means.

Annular snap 307, which is made of a resilient material, preferably a resilient medical grade plastic, is a unitary member shaped to include an annular bottom wall 309, an annular top wall 311 and a circular side wall 313, side wall 313 interconnecting bottom wall 309 and top wall 311. Bottom wall 309 is shaped to define an opening 315, opening 315 being sized so that bottom wall 309 may be advanced over that portion of tube 45 below flange 49 (as well as that portion of a gastrostomy feeding tube inserted over said portion of tube 45). Top wall 311 is shaped to define an opening 317, opening 317 being sized so that wall 311 may be advanced over that portion of tube 45 below flange 49 (as well as any overlying gastrostomy feeding tube) and then may be flexed for advancement past flange 49, thereafter snapping back to its un-flexed state where it is retained against withdrawal by flange 49.

Figure 19:
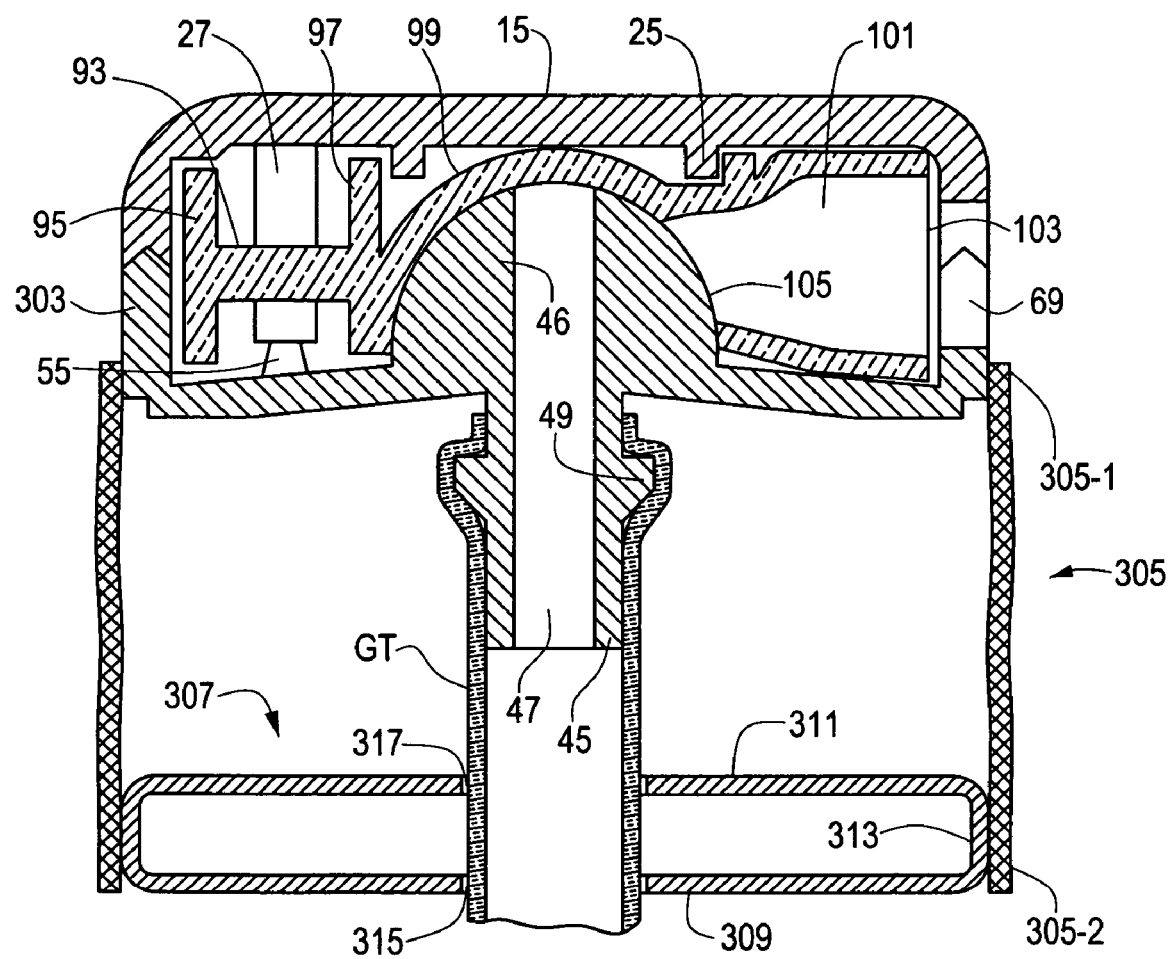
FIG. 19 is a section view of the low profile adaptor of FIG. 18, said low profile adaptor being shown in an expanded state with the proximal end of a gastrostomy feeding tube inserted over the tube flange.
Figure 20:
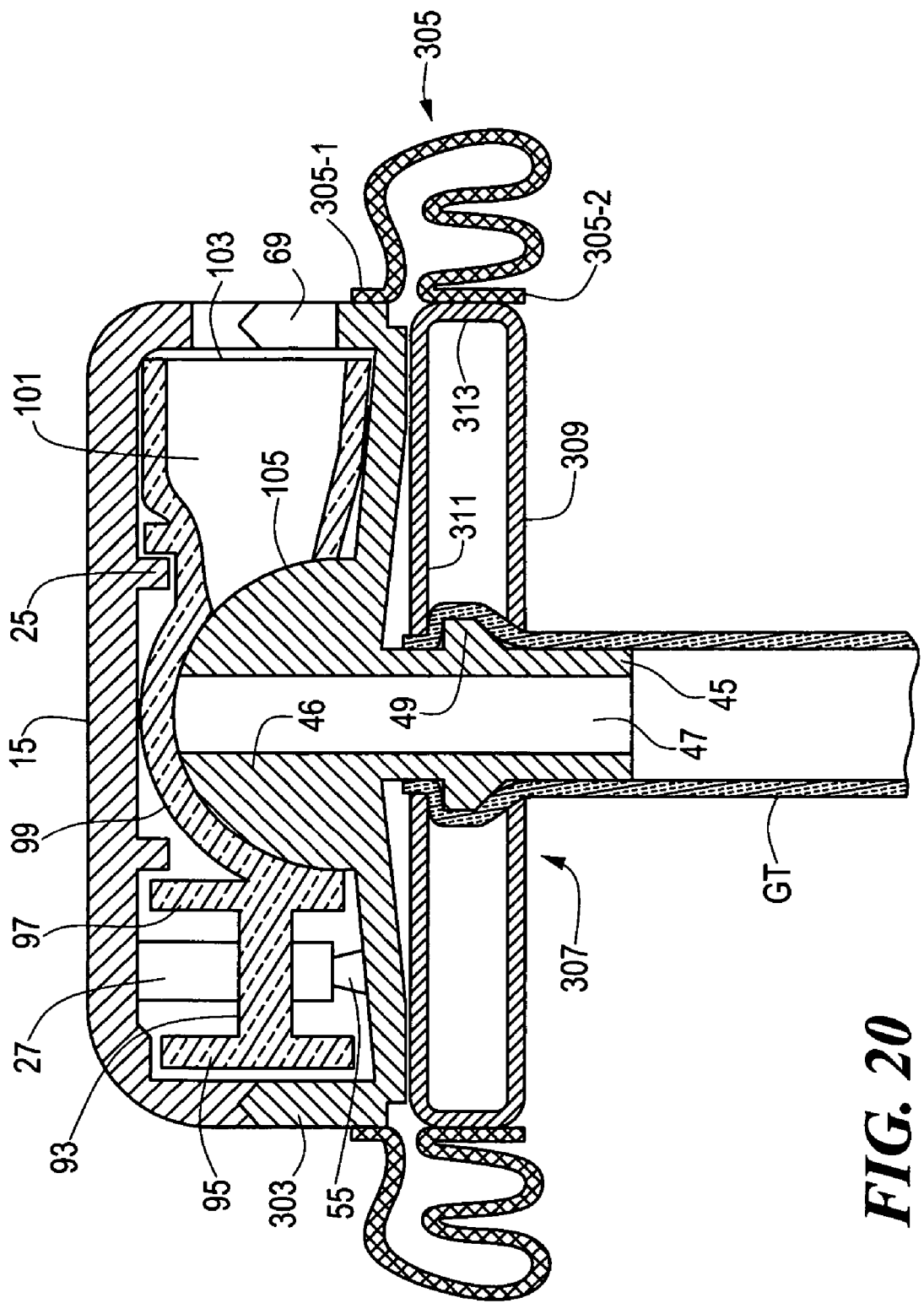
FIG. 20 is a section view of the low profile adaptor of FIG. 18, said low profile adaptor being shown in a contracted state with the proximal end of a gastrostomy feeding tube secured to the tube flange using the annular snap.

One may install adaptor 301 on a patient as follows: First, referring to FIG. 19, the proximal end of an implanted gastrostomy feeding tube GT that has been cut to its desired length is inserted up through openings 315 and 317 of snap 307 and is then inserted over tube 45 until it is advanced past flange 49. Then, referring to FIG. 20, snap 307 is moved upwardly until top wall 311 of snap 307 has been advanced, through flexion, completely past flange 49, whereby snap 307 serves to securely clamp gastrostomy feeding tube GT against flange 49. As seen in FIG. 20, the upward movement of snap 307 results in the compression of tubing 305 and the formation of a plurality of folds therein. Where tubing 305 is made of silicone rubber or the like, such folds may provide a soft interface with the patient's skin. (If desired, other portions of adaptor 301 may additionally be covered with a layer of silicone rubber also for providing a soft interface with the patient's skin.) Thus installed, adaptor 301 may be used in the same manner as adaptor 11. It may be noted that adaptor 301 has a retentive force, or grip strength, on tube GT of at least approximately 17 pounds.

It should be noted that the step of advancing snap 307 past flange 49 may be performed using only one hand.

As can be appreciated, one distinction between adaptor 301 and adaptor 201 is that adaptor 301 does not require the assembly of any of its components prior to its installation since snap 307 is tethered by tubing 305 to the remainder of adaptor 301. All that is required for installation is that the gastrostomy feeding tube be inserted past flange 49 of adaptor 301 and that adaptor 301 then be compressed in the manner described above so that snap 307 clamps the gastrostomy feeding tube against flange 49.

Although the adaptors described herein are said to be designed for low profile use with gastrostomy feeding tubes, it should be understood that said adaptors are not limited to low profile use and could be used with gastrostomy feeding tubes in a high profile arrangement. Moreover, apart from whether the present adaptors are used in a low profile or high profile context, the present adaptors are not limited to use with gastrostomy feeding tubes and may be used with various other medical catheters, such as jejunostomy feeding tubes or enteral feeding tubes. Furthermore, in addition to being used for feeding, the present adaptors could also be used for drainage.

It should also be understood that the adaptors of the present invention could be modified to utilize alternate axes of rotation for the switch mechanism or to utilize alternate flow switch configurations, such as pop-tops.

The embodiments of the present invention recited herein are intended to be merely exemplary and those skilled in the art will be able to make numerous variations and modifications to it without departing from the spirit of the present invention. All such variations and modifications are intended to be within the scope of the present invention as defined by the claims appended hereto.

What is claimed is:

1. An adaptor for use with a medical catheter, said adaptor comprising:
   a housing comprising a first tubular channel adapted to connect to a proximal end of a medical catheter, said first tubular channel having a first longitudinal axis;
   a dial comprising a second tubular channel having a second longitudinal axis, said dial mounted in the housing such that the first longitudinal axis is the center of rotation of the dial, said first longitudinal axis being distinct from the second longitudinal axis; and
   an adaptor fitting having a distal end removably connected to the second tubular channel, and a proximal end adapted to connect to an external tube;
   said dial being rotatable between an open position and a closed position when the adaptor fitting is connected thereto, wherein in the open position the first tubular channel is fluidly connected to the second tubular channel, and in the closed position the first tubular channel is not fluidly connected to the second tubular channel,
   said dial not being rotatable between an open position and a closed position when the adaptor fitting is not connected thereto.

2. The adaptor of claim 1, wherein said housing comprises an upper housing member, an intermediate housing member, and a lower housing member.

3. The adaptor of claim 2, wherein the dial is rotatably mounted between the upper housing member and the intermediate housing member.

4. The adaptor of claim 1, wherein said first longitudinal axis is perpendicular to the second longitudinal axis.

5. The adaptor of claim 1, wherein the second longitudinal axis is not the center of rotation of the dial.

6. An adaptor for use with a medical catheter, said adaptor comprising:
   a housing comprising a first tubular channel adapted to connect to a proximal end of a medical catheter, said first tubular channel having a first longitudinal axis;
   a dial comprising a second tubular channel having a second longitudinal axis, said dial mounted in the housing such that the dial is rotatable about the first longitudinal axis, said first longitudinal axis being distinct from the second longitudinal axis; and
   an adaptor fitting having a distal end removably connected to the second tubular channel, and a proximal end adapted to connect to an external tube;
   said dial being rotatable between an open position and a closed position when the adaptor fitting is connected thereto, wherein in the open position the first tubular channel is fluidly connected to the second tubular channel, and in the closed position the first tubular channel is not fluidly connected to the second tubular channel, wherein said housing comprises an upper housing member, an intermediate housing member, and a lower housing member, and wherein said intermediate housing member comprises a generally circular bottom wall, a side wall, and an open top.

7. The adaptor of claim 6, said intermediate housing member further comprising the first tubular channel, said first tubular channel extending transversely upwardly and downwardly from a center of the bottom wall.

8. The adaptor of claim 7, wherein a lower portion of the first tubular channel includes an annular flange.

9. The adaptor of claim 8, said lower housing member comprising a generally circular bottom wall, a side wall, an open top, a central opening in the bottom wall, and a sleeve extending upwardly from the central opening, said sleeve receiving said annular flange therein.

10. The adaptor of claim 9, wherein a proximal end of a medical catheter is adapted to be secured between the annular flange and the sleeve.

11. The adaptor of claim 7, wherein an upper portion of the first tubular channel is dome-shaped and includes a lateral slot, and wherein in the open position the lateral slot is aligned with the second tubular channel.

12. The adaptor of claim 11, said upper housing member comprises a generally circular top wall, a side wall, an open bottom, and a circular ridge on the bottom surface of the top wall, said circular ridge for receiving the dome-shaped upper portion of the first tubular channel therein.

13. The adaptor of claim 6, said intermediate housing member further comprising a plurality of resilient legs extending downwardly from a bottom surface of the bottom wall.

14. An adaptor for use with a medical catheter, said adaptor comprising:
a housing comprising a first tubular channel adapted to connect to a proximal end of a medical catheter, said first tubular channel having a first longitudinal axis;
a dial comprising a second tubular channel having a second longitudinal axis, said dial mounted in the housing such that the dial is rotatable about the first longitudinal axis, said first longitudinal axis being distinct from the second longitudinal axis; and
an adaptor fitting having a distal end removably connected to the second tubular channel, and a proximal end adapted to connect to an external tube;
said dial being rotatable between an open position and a closed position when the adaptor fitting is connected thereto, wherein in the open position the first tubular channel is fluidly connected to the second tubular channel, and in the closed position the first tubular channel is not fluidly connected to the second tubular channel,
wherein said housing comprises an upper housing member, an intermediate housing member, and a lower housing member, and
wherein said lower housing member comprises a generally circular bottom wall, a side wall, an open top, and a central opening in the bottom wall.

15. The adaptor of claim 14, said lower housing member further comprising a plurality of posts extending upwardly from a top surface of the bottom wall, each post having a cavity therein.

16. The adaptor of claim 15, said intermediate housing member comprising a generally circular bottom wall, a side wall, an open top, and a plurality of resilient legs extending downwardly from a bottom surface of the bottom wall, each leg adapted to be received within the cavity of each post.

17. An adaptor for use with a medical catheter, said adaptor comprising:
a housing comprising a first tubular channel adapted to connect to a proximal end of a medical catheter, said first tubular channel having a first longitudinal axis;
a dial comprising a second tubular channel having a second longitudinal axis, said dial mounted in the housing such that the dial is rotatable about the first longitudinal axis, said first longitudinal axis being distinct from the second longitudinal axis; and
an adaptor fitting having a distal end removably connected to the second tubular channel, and a proximal end adapted to connect to an external tube;
said dial being rotatable between an open position and a closed position when the adaptor fitting is connected thereto, wherein in the open position the first tubular channel is fluidly connected to the second tubular channel, and in the closed position the first tubular channel is not fluidly connected to the second tubular channel,
wherein said housing comprises an upper housing member, an intermediate housing member, and a lower housing member, and
wherein said upper housing member comprises a generally circular top wall, a side wall, an open bottom, and a circular ridge on the bottom surface of the top wall.

* * * * *